(12) United States Patent
Grandfield et al.

(10) Patent No.: US 10,939,931 B2
(45) Date of Patent: Mar. 9, 2021

(54) EMBOLECTOMY DEVICE HAVING MULTIPLE EMBOLECTOMY STRUCTURES

(71) Applicants: STRYKER CORPORATION, Kalamazoo, MI (US); STRYKER EUROPEAN HOLDINGS I, LLC, Kalamazoo, MI (US)

(72) Inventors: Ryan Matthew Grandfield, Livermore, CA (US); Aleksandr Leynov, Walnut Creek, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 186 days.

(21) Appl. No.: 16/012,426

(22) Filed: Jun. 19, 2018

(65) Prior Publication Data

US 2019/0380723 A1 Dec. 19, 2019

(51) Int. Cl.
*A61B 17/221* (2006.01)
*A61F 2/01* (2006.01)
*A61B 17/22* (2006.01)

(52) U.S. Cl.
CPC .............. *A61B 17/221* (2013.01); *A61F 2/01* (2013.01); *A61B 2017/2215* (2013.01); *A61B 2017/22034* (2013.01); *A61F 2002/016* (2013.01)

(58) Field of Classification Search
CPC ...... A61F 2002/016; A61F 2002/91558; A61F 2/01–012; A61F 2/016; A61F 2/018; A61B 17/221; A61B 2017/22034; A61B 2017/2215; A61B 17/320725; A61B 2017/2217; A61B 17/22031; A61B 17/22032
See application file for complete search history.

(56) References Cited

U.S. PATENT DOCUMENTS

| 6,059,810 | A  | * | 5/2000 | Brown ..................... A61F 2/86 606/192 |
| 8,460,313 | B2 | * | 6/2013 | Huffmaster .......... A61B 17/221 604/104 |
| 8,529,596 | B2 |   | 9/2013 | Grandfield et al. |

(Continued)

OTHER PUBLICATIONS

PCT International Search Report and Written Opinion for U.S. Appln. No. PCT/US2019/037265, Applicant Stryker Corporation, dated Aug. 22, 2019 (10 pages).

*Primary Examiner* — Katherine H Schwiker
*Assistant Examiner* — Alexis D Amechi
(74) *Attorney, Agent, or Firm* — Vista IP Law Group, LLP

(57) ABSTRACT

An embolectomy device includes a pair of elongate spine members extending in a substantially parallel configuration along a longitudinal axis of the device, a first plurality of clot engaging structures having first ends attached to a first one of the spine members and second ends attached to other one of the spine members, and a second plurality of clot engaging structures having first and second ends attached to the respective first and second spine members offset 180° from the first plurality of attached clot engaging structures, such that, when the embolectomy device is unsheathed within in a blood vessel alongside a clot, one of the first and second plurality of the clot engaging structures contact and compress against a wall of the blood vessel to provide a biasing force to facilitate engagement of the other one of the first and second plurality of the clot engaging structures with the clot.

8 Claims, 19 Drawing Sheets

(56) References Cited

U.S. PATENT DOCUMENTS

| | | |
|---|---|---|
| 8,852,205 B2 | 10/2014 | Brady et al. |
| 2013/0131690 A1 | 5/2013 | Nagl et al. |
| 2013/0345739 A1* | 12/2013 | Brady .................. A61B 17/221 |
| | | 606/200 |
| 2016/0143653 A1 | 5/2016 | Vale et al. |
| 2016/0256255 A9 | 9/2016 | Ma |
| 2018/0056051 A1 | 3/2018 | Kabra |

* cited by examiner

EMBOLECTOMY DEVICE HAVING MULTIPLE EMBOLECTOMY STRUCTURES

FIELD

The inventions disclosed herein relate generally to medical devices configured for removing embolic obstructions from the vasculature system.

BACKGROUND

Blood thrombus, embolus or clots may occur in a person's vasculature system. Sometimes such clots are harmlessly dissolved in the blood stream. Other times, however, such clots may lodge within a neurovascular blood vessel lumen (i.e., downstream from the carotid arteries), where the clots can partially or completely occlude the flow of blood, referred to as an "ischemic event". If the partially or completely occluded vessel feeds blood to sensitive tissue such as, the brain, lungs or heart, serious tissue damage may result. Such ischemic events may be exacerbated by atherosclerosis, a vascular disease that causes the vessels to become narrowed and/or tortuous. The narrowing and/or increased tortuousness of the blood vessels may, in certain circumstances, lead to the formation of atherosclerotic plaque that can cause further complications.

Known embolectomy devices may be used in a variety of applications to remove blood clots or other foreign bodies from blood vessels. Such devices includes ones cylindrical scaffold embolectomy devices, such those illustrated and described in U.S. Pat. No. 8,529,596 to Grandfield, which is fully incorporated herein by reference. Further, embolectomy devices may include a plurality of scaffolds, such as having an inner cylindrical scaffold concentrically disposed within an outer engaging "stent-basket", or having a plurality of adjacently disposed inner cylindrical scaffolds, as those illustrated and described in U.S. Pat. No. 8,852,205, which is fully incorporated herein by reference.

FIGS. 1A-B illustrate an exemplary prior art embolectomy device 12 that is manufactured and sold by the Neurovascular Division of Stryker Corporation (http://www.stryker.com/en-us/products/NeurovascularIntervention/index.htm). FIG. 1A shows the embolectomy device 12 in a two-dimensional plane view, and FIG. 1B shows the device 12 a three-dimensional expanded tubular configuration. The embolectomy device 12 is composed of shape memory, self-expandable and biocompatible materials, such as Nitinol. The embolectomy device 12 is preferably manufactured by laser cutting a tube or a sheet of shape memory material. The embolectomy device 12 is coupled to an elongate flexible wire 40 that extends proximally from device 12; the wire 40 is configured to push and pull the embolectomy device 12 through sheaths and/or catheters into a target site in a blood vessel.

As shown in FIG. 1A, the embolectomy device 12 includes a includes a proximal end portion 14, a main body portion 16 and a distal end portion 18, the main body portion including a plurality of longitudinal undulating elements 24 (e.g., wires, struts) with adjacent undulating elements being out-of-phase with one another and connected in a manner to form a plurality of diagonally disposed cell structures 26 extending between the respective proximal and distal end portions of the device. The cell structures 26 in the main body portion 16 and distal end portion 18 of the embolectomy device 12 extend continuously and circumferentially around a longitudinal axis 30 of the device 12 (FIGS. 1A-B).

In particular, the cell structures 26 in the proximal end portion 14 extend less than circumferentially around the longitudinal axis 30 of the device 12. The dimensional and material characteristics of the cell structures 26 of the main body portion 16 are selected to produce sufficient radial force (e.g., radial force per unit length of between 0.005 N/mm to 0.100 N/mm, preferable between 0.040 N/mm to 0.080 N/mm when the outer diameter of the main body portion is between 1.0 mm to 1.5 mm) and contact interaction to cause the cell structures 26, and/or the elements 24, to engage with an embolic obstruction residing in the vasculature in a manner that permits partial or full removal of the embolic obstruction from the patient. The out-of-phase configuration of the diagonally disposed cell structures 26 of the device 12 allows distribution of the radial force along the body portion 16, such that the elements 24 engage the obstruction and/or contact the vessel walls in a spiral or non-symmetrical manner, as depicted in FIG. 2, instead of in an annular or symmetrical manner.

As best seen in FIG. 1B, the embolectomy device 12 has an overall length L1 of about 32 millimeters with the main body portion 16 length L2 measuring about 20 millimeters. Usually, the length of the main body portion 16 is generally between about 2.5 to about 3.5 times greater than the length of the proximal end portion 14.

FIG. 2 illustrates the embolectomy device 12 of FIGS. 1A-B disposed in a target site of a tortuous vascular anatomy of a patient capturing an embolic obstruction or clot 75. In an unexpanded or radially compressed configuration (not shown), such as when the embolectomy device 12 is disposed within a delivery catheter 80, the embolectomy device 12 has an unexpanded outer diameter (UOD) between 0.4 to 0.7 millimeters. In a radially expanded configuration (FIGS. 1B-2), the embolectomy device 12 has an expanded outer diameter (EOD) between 2.5 to 5.0 millimeters. The embolectomy device 12 produces sufficient radial force and contact interaction to cause the strut elements 24 and/or cell structures 26 to engage/snare/encapsulate/capture/pinch and/or entrap the embolic obstruction 75 disposed within the blood vessel 70, allowing removal of the embolic obstruction 75 from the patient. The diameter of the main body portion 16 in a fully expanded configuration is about 4.0 millimeters with the cell pattern, elements 24 dimensions and material being selected to produce a radial force of between 0.040 N/mm to 0.050 N/mm when the diameter of the main body portion is reduced to between 1.0 millimeters to 1.5 millimeters. The cell pattern 26, strut dimensions 24 and material(s) are selected to produce a radial force of between 0.010 N/mm to 0.035 N/mm when the diameter of the main body portion 16 is reduced to 3.0 millimeters.

Regardless of the technique used to manufacture the embolectomy device 12, the manner in which the strut elements 24 interconnect determines the device's longitudinal and radial rigidity and flexibility. Radial rigidity is needed to provide the radial force needed to engage the clot or embolic obstruction 75, but radial flexibility is needed to facilitate radial compression of the device 12 for delivery into a target site. Longitudinal rigidity is needed to pull an engaged clot or embolic obstruction 75 from the blood vessel 70, but longitudinal flexibility is needed to facilitate delivery of the device 12 (e.g., through tortuous vasculature). Embolectomy device 12 patterns are typically designed to maintain an optimal balance between longitudinal and radial rigidity and flexibility for the device 12. However, in certain applications, after deployment of the device 12 into the blood vessel 70, and once the embolectomy device 12 is subjected to tension force for retraction or withdrawal, the device 12, particularly, the main body portion 16, tends to stretch creating a smaller profile or outer diameter (OD), similar to the unexpanded outer diameter (UOD) described above (e.g., between 0.4 to 0.7 millimeters).

FIG. 3A illustrates the embolectomy device 12 of FIGS. 1A-B and 2, disposed in a blood vessel 70 distally located from the catheter 80 and having a smaller profile/OD. The stretching of the device 12 and smaller profile/OD may cause the device 12 to be withdrawn past the embolic obstruction 75 without engaging or capturing the obstruction 75, as shown in FIGS. 3A and 3C-G. FIG. 3B-G are cross-sectional views of the blood vessel 70 having a lumen 72 with the embolic obstruction 75 therein. In an embolectomy procedure for removing the embolic obstruction 75 from the blood vessel lumen 72, the delivery catheter 80 is advanced through the lumen 72, until the distal portion of the catheter 80 is disposed in a target site adjacent to the obstruction 75, with the radially compressed embolectomy device 12 disposed within the catheter 80, as shown in FIG. 3C. The embolectomy device 12 is then pushed distally relative to the catheter 80, or the catheter 80 is withdrawn proximally relative to the embolectomy device 12 (or some of each), in order to deploy the device 12 out of the catheter 80 and into the blood vessel lumen 72, allowing the no-longer radially constrained embolectomy device 12 to radially expand within the blood vessel lumen 72 in order to engage, ensnare and capture the obstruction 75.

However, in certain applications (e.g., hard/dense embolic obstruction 75) the radial expansion force 33 of embolectomy device 12 is not sufficient to overcome the hardness and resistive force 36 of the embolic obstruction 75 to allow the struts of device 12 to penetrate into and integrate with the clot 75 minimizing the device 12 outward expansion, as shown in FIG. 3D, or causing the device 12 to take the path of least resistance by extending around the obstruction 75, as shown in FIG. 3E. In other applications, when the radial expansion force 33 exerts and expands the embolectomy device 12, some push 31 and pull 32 forces act and react during the expansion of the device 12, such that not sufficient forces are directed or created to overcome the resistive force 36 of the embolic obstruction 75, as shown in FIG. 3F. Normally, these forces 31/32 in the device 12 allow for a partial or insufficient penetration and/or integration of the struts of device 12 with the obstruction 75, as shown in FIG. 3G. The undesirable minimally expanded profile/OD (FIG. 3D), the elongated profile/OD extending around the obstruction 75 (FIG. 3E) or the less than suitable expansion of the device 12 minimally engaging the obstruction 75 (FIGS. 3F-G) produces none to minimal penetration, integration, engagement and/or ensnaring of the device 12 with the obstruction 75, which tends to pass or leave behind the embolic obstruction 75 without capturing and/or removing the obstruction 75 when the device 12 is withdrawn.

SUMMARY

Embodiments of the disclosed inventions are directed to an embolectomy device biased to expand from a radially constrained configuration to a radially expanded configuration when released from a delivery catheter into a blood vessel, the embolectomy device including first and second elongate spine members arranged in a substantially parallel relationship extending along a longitudinal axis of the embolectomy device, a first plurality of clot engaging structures have first end attached to the first elongate spine member and a second end attached to the second elongate spine member, and a second plurality of clot engaging structures, each clot engaging structure of the second plurality having a first end attached to the first elongate spine member at a location in which the first end of a corresponding clot engaging structure of the first plurality is attached to the first elongate spine member, and a second end attached to the second elongate spine member at a location in which the second end of the corresponding clot engaging structure of the first plurality is attached to the second elongate spine member, wherein the respective clot engaging structures of the first plurality and of the second plurality are resilient and configured such that, when the embolectomy device is unsheathed within in a blood vessel alongside a clot, the clot engaging structures of one of the first and second plurality contact and compress against a wall of the blood vessel to provide a biasing force to facilitate engagement of the clot engaging structures of the other one of the first and second plurality with the clot.

In one embodiment, middle portion of each clot engaging structure of the first and second pluralities have a chevron/furcula-like configuration. By way of example and without limitation, the middle portions of the first plurality of clot engaging structures may form a first succession of substantially aligned peaks extending radially outwardly along the longitudinal axis of the embolectomy device, and the middle portions of the second plurality of clot engaging structures may form a second succession of substantially aligned peaks extending radially outwardly along the longitudinal axis of the embolectomy device, respectively, when the embolectomy device is in the radially expanded configuration, wherein the peaks of the first succession may be circumferentially offset approximately 180° from the peaks of the second succession. In some such embodiments, the peaks may be jaw-shaped.

In various embodiments, the clot engaging structures of first and second pluralities may have arcuate or non-arcuate configurations.

In various embodiments, the clot engaging structures of the first plurality may be aligned with the clot engaging structures of the second plurality.

In various embodiments, the embolectomy device includes a pusher wire, wherein the each of the first and second elongate spine members are attached to a distal end portion of the push wire.

In various embodiments, the first and second elongate spine members are composed of a stretch-resistant material and are configured such that, when the embolectomy device is translated proximately within the blood vessel, the respective first and second pluralities of clot engaging structures are simultaneously translated proximately with the first and second elongate spine members for facilitating engagement of the clot engaging structures with the clot.

In various embodiments, the first and second elongate spine members are configured to bend and align the embolectomy device along a longitudinal neutral axis as the device is translated, advanced or withdrawn within the delivery catheter or within the blood vessel, wherein the alignment of the embolectomy device by the first and second elongate spine members preferably allows for alignment of respective clot engaging structures with the clot when the embolectomy device is deployed within the blood vessel proximately to the clot. Preferably, the alignment of the clot respective engaging structures with the clot is maintained as the device is translated proximately to remove the clot from the blood vessel.

Other and further aspects and features of embodiments of the disclosed inventions will become apparent from the ensuing detailed description in view of the accompanying figures.

DETAILED DESCRIPTION OF THE ILLUSTRATED EMBODIMENTS

Figure 1A:
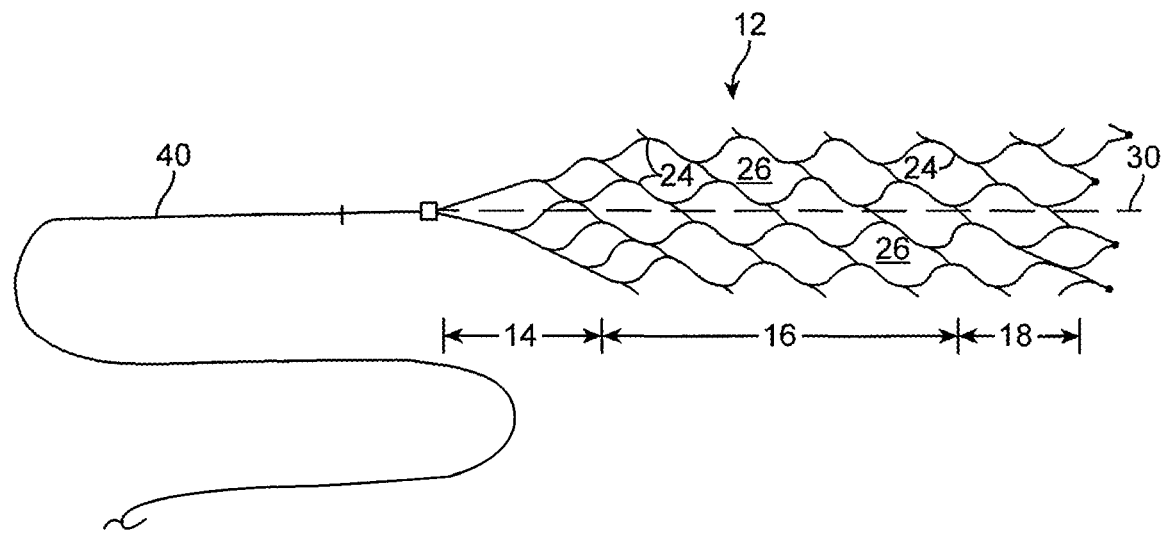
FIGS. 1A-1B are perspective views of a prior art embolectomy device.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 4:
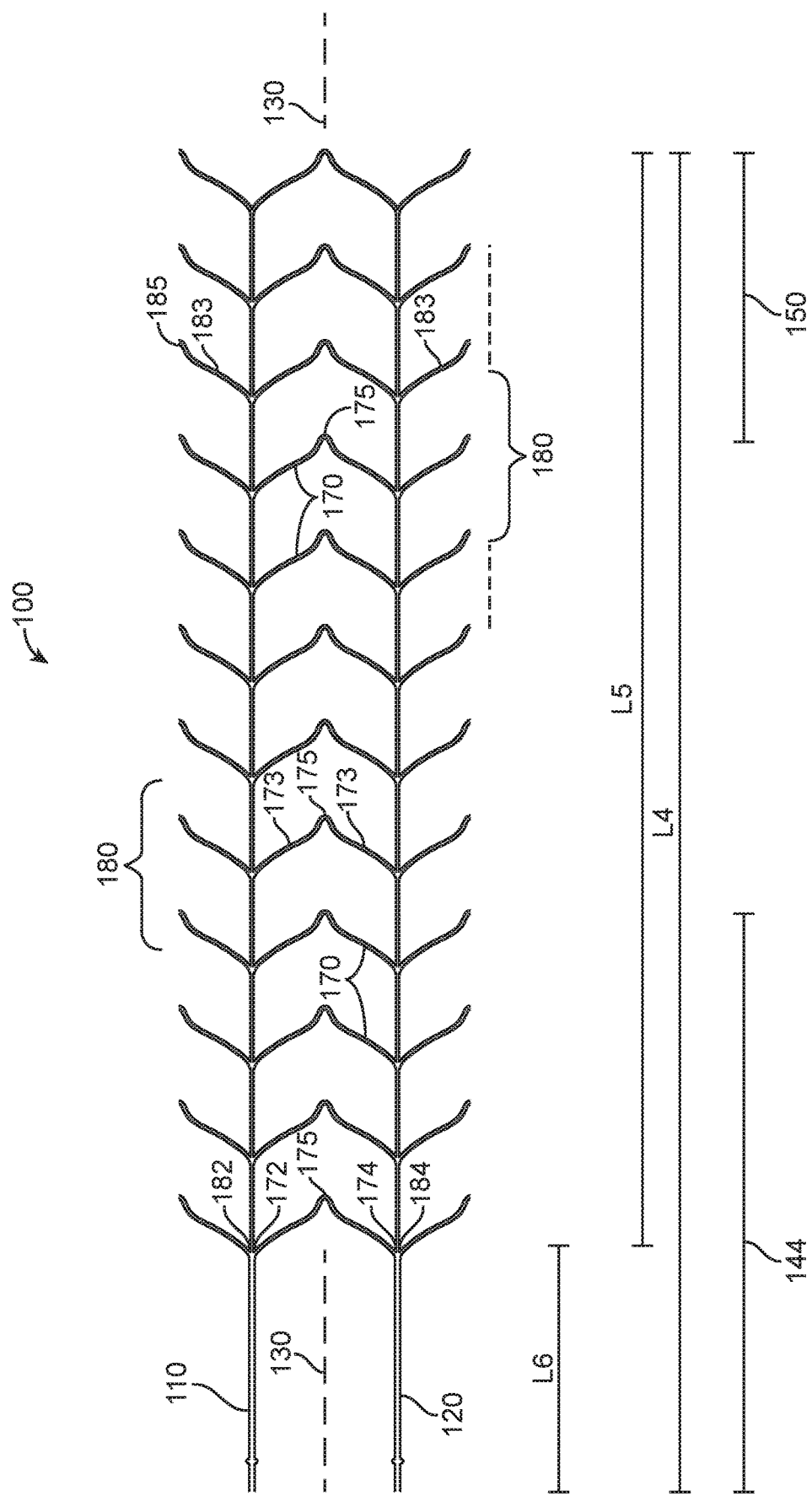
FIG. 4 is a planar and cross-sectional view of an exemplary embolectomy device constructed according to one embodiment of the disclosed inventions.

FIGS. 4-7 illustrate an elongate embolectomy device 100, constructed in accordance with one embodiment of the disclosed inventions. FIG. 4 depicts the embolectomy device 100 in a two-dimensional plane view, such as if the device were laid flat on a surface. The embolectomy device 100 may be formed of a unitary component (e.g., laser cut of flat sheet or cylindrical, tubular structure, 3D printing, extrusion or the like), or may also include separate components that are welded, bonded or otherwise coupled to one another. By way of non-limiting example of the device when formed of a unitary component, the two-dimensional plane view of FIG. 4 may be used as a cut pattern; such as, placing the pattern over and/or around a tubular structure to manufacture the embolectomy device 100 by laser cutting said pattern into the tubular structure. Further, as used in this specification, the term "coupled" may refer to one or more components that may be directly or indirectly attached, secured, or otherwise, connected. The embolectomy device 100 comprises self-expanding and/or shape memory materials, such as Nitinol, or other suitable materials or combinations thereof (e.g., stainless steel, titanium, platinum, nickel, tantalum, chrome cobalt alloy, or the like). The embolectomy device 100 may be composed of wires, struts, bundle of wires, drawn-filled tubes, or the like. The embolectomy device 100 may include radio-opaque markers or be coated with a layer of radiopaque materials.

As shown in FIG. 4, the embolectomy device 100 includes a proximal portion 144, a distal portion 150, and a longitudinal axis 130 extending therebetween. The embolectomy device 100 having a first elongate spine member 110 extending along the longitudinal axis 130, and a second elongate spine member 120 extending along the longitudinal axis 130 and disposed substantially parallel to the first elongate spine 110. The embolectomy device 100 having a first plurality of clot engaging structures 170, each clot engaging structure 170 of the first plurality 170 having a first end 172 attached to the first elongate spine member 110 and a second end 174 attached to the second elongate spine member 120. The embolectomy device 100 further having a second plurality of clot engaging structures 180, each clot engaging structure 180 of the second plurality having a first end 182 attached to the first elongate spine member 110 at a location in which the first end 172 of a corresponding clot engaging structure 170 of the first plurality is attached to the first elongate spine member 100, and a second end 184 attached to the second elongate spine member 120 at a location in which the second end 174 of the corresponding clot engaging structure of the first plurality 170 is attached to the second elongate spine member 120.

In the embodiment of FIG. 4, the first elongate spine member 110 and the second elongate spine member 120, each have an overall length L4 of approximately 32 millimeters with respective active portions length L5 measuring approximately 30 millimeters, and a proximal end portion L6. The active portion length L5 of the spine members 110 and 120 includes the first and second plurality of clot engaging structures 170, 180. The first elongate spine member 110 and the second elongate spine member 120 are composed of suitable stretch-resistance material having substantially the same mass (e.g., width and/or thickness) along their respective length L4. In some embodiments, the mass (e.g., width and/or thickness) along the respective length L4 of the first and/or second elongate spine members 110, 120 may vary. For example, the first and/or second elongate spine members 110, 120 may be thicker and/or wider around the proximal portion 144 of the embolectomy device 100 compared to width and/or thickness around the distal portion 150 of the embolectomy device 100. Further, the cross-sectional views along the respective length L4 of the first and/or second elongate spine members 110, 120 may include round, oval, square or any other suitable cross-sectional configuration or combination thereof. The proximal end portion L6 includes the respective proximal ends of the first and second elongates spine members 110 and 120 that when coupled together form the antenna 115, as shown in FIGS. 5-8. The proximal end portion L6 measures approximately 0.1 to 1.0 millimeters.

By way of non-limiting example, the embolectomy device 100 includes clot engaging structures 170 in the first plurality of structures 170, and clot engaging structures 180 in the second plurality of structures 180, as shown in FIG. 4. However, it should be appreciated than the first and second plurality of structures 170 and 180 may have between 5 to 45 clot engaging structures, each extending along the length L5 or attached to the respective first and second elongate spine members 110, 120. The cross-sectional views along the length of one or more of the clot engaging structure 170 and/or 180 may be include a continuous configuration or may vary along their respective length. For example, a cross-section of one of the clot engaging structure 170 can be circular in a first portion and can be oval in a second portion (not shown). Further, the cross-sectional views along the along the length of one or more of the clot engaging structure 170 and/or 180 may include round, oval, square or any other suitable cross-sectional configuration or combination thereof.

Figure 5:
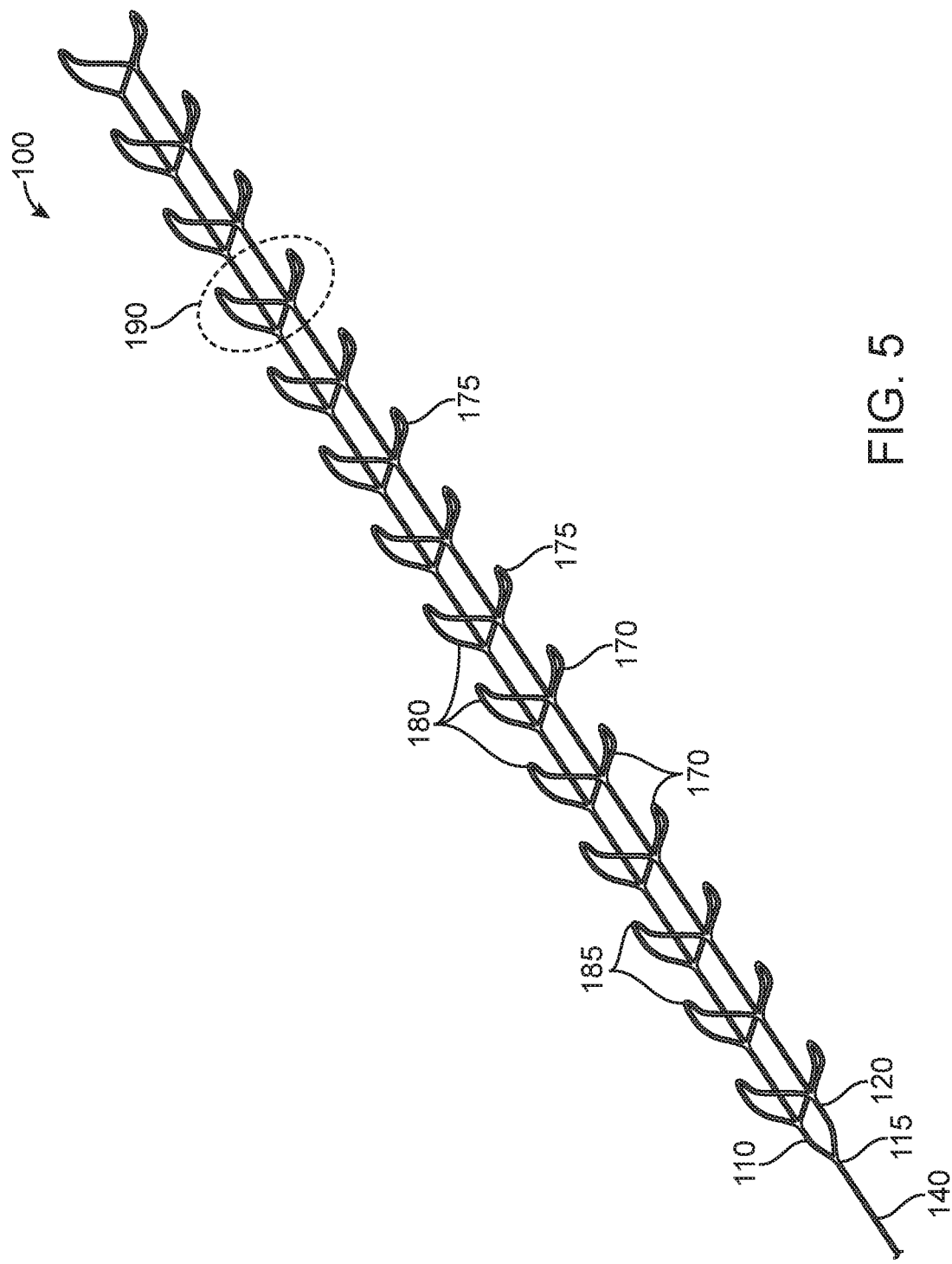
FIGS. 5-7 are perspective views of the device of FIG. 4, according to the disclosed inventions.
Figure 6:
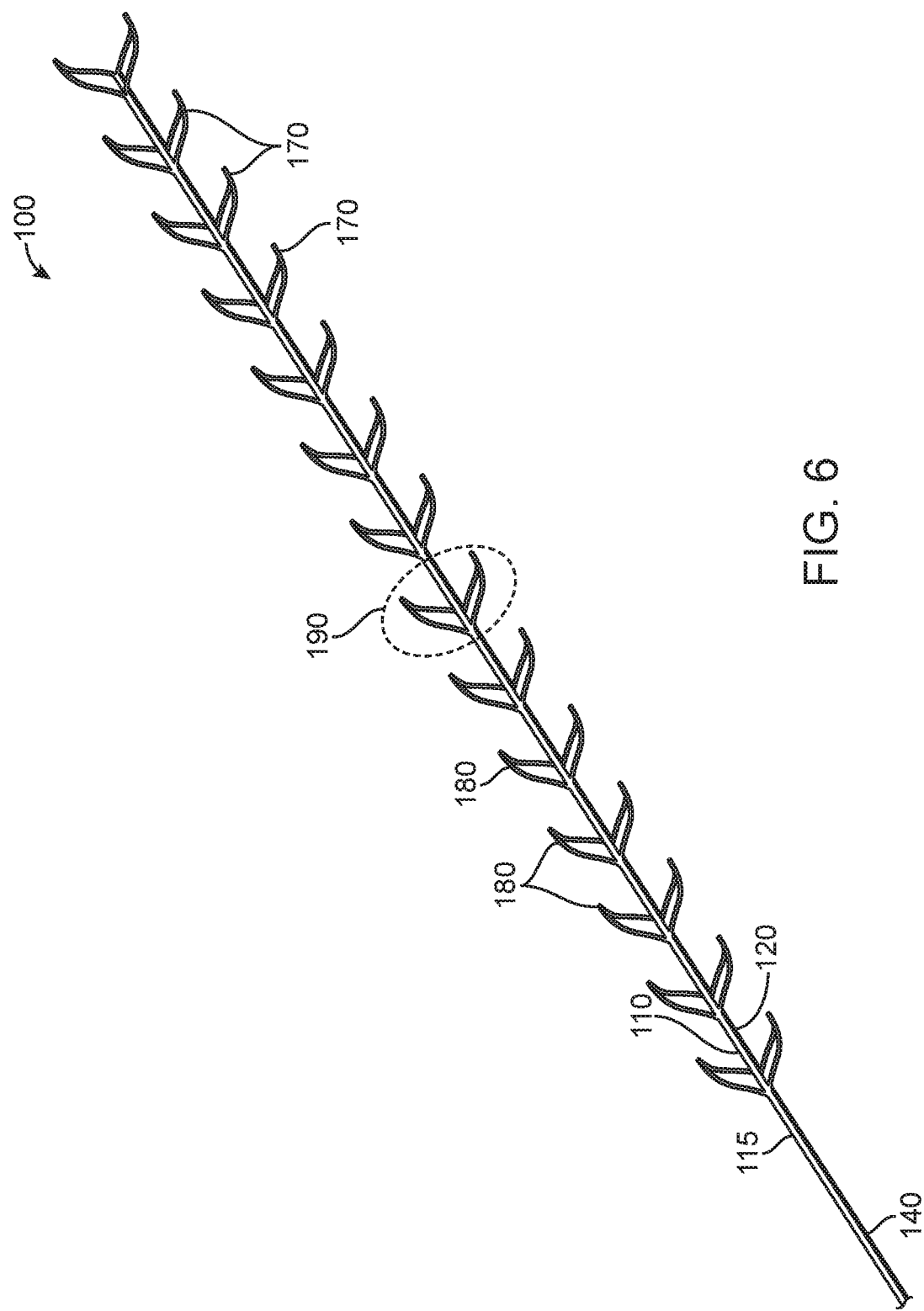
Figure 7:
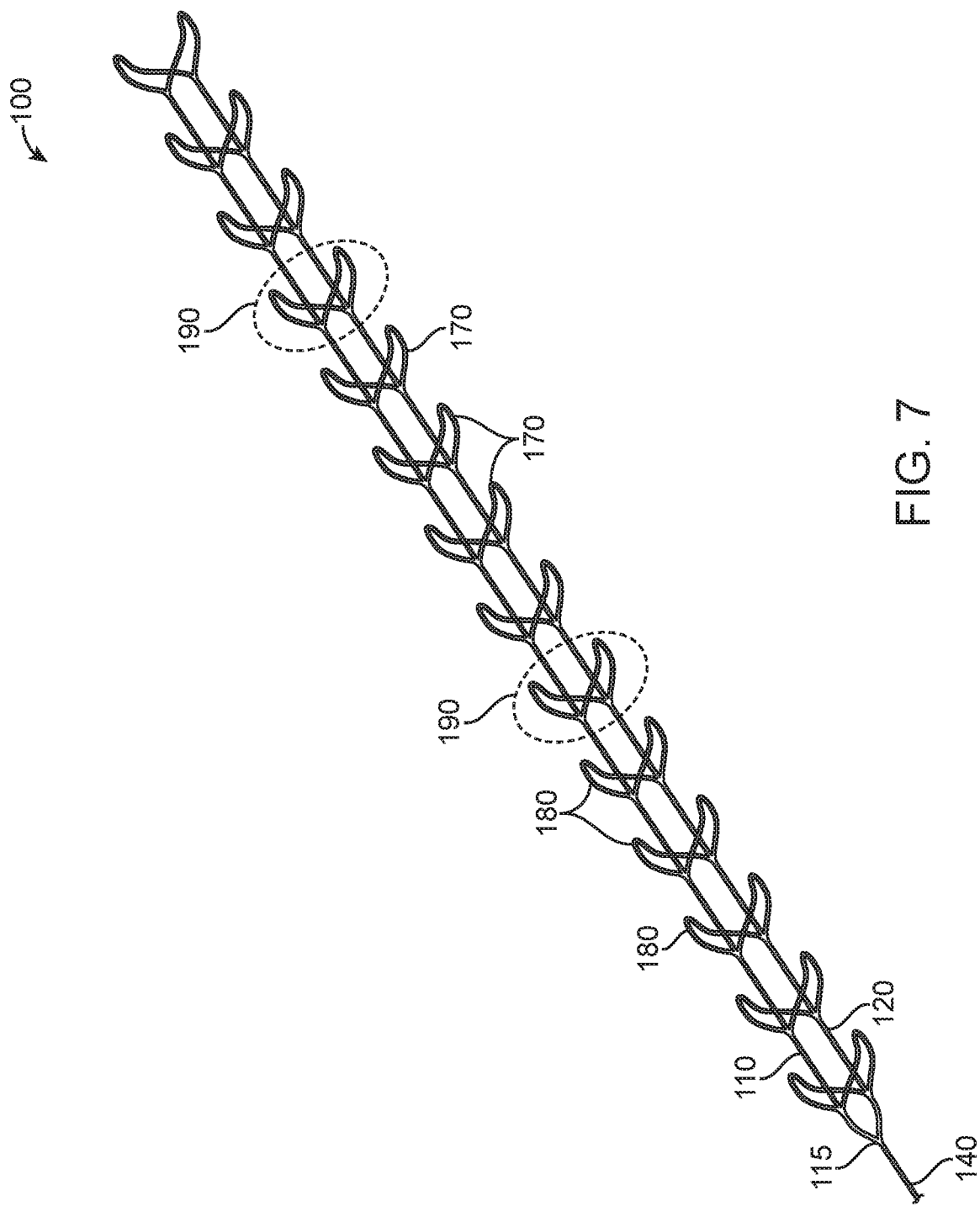

Each of the first plurality of clot engaging structure 170 comprises a chevron/furcula-like configuration, having respective curved regions 173 and a pointed region 175 therebetween, as shown in FIG. 4. Each of the curve regions 173 terminate in respective first or second ends 172, 174 of each of the clot engaging structure 170. Further, each of the second plurality of clot engaging structure 180 have respective curved regions 183, such that when the two-dimensional plane view of the embolectomy device 100 of FIG. 4 is formed into a three-dimensional configuration, as shown in FIGS. 5-7, the curved regions 183 are coupled (e.g., solder, weld, adhesive, or other suitable attachment methods) to each other forming respective pointed regions 185. The chevron/furcula-like configuration of the first and second plurality of clot engaging structures 170, 180 assists, allows, or maintains the position of the second elongate spine member 120 to be substantially parallel with respect to the first elongate spine member 110, as it will be described in further detailed below. It should be further appreciated that the embolectomy device 100 may have alternative shapes, and other suitable configurations of the first and second plurality of clot engaging structures 170, 180 configured to assist, allow or maintain the substantially parallel disposition of the first and second elongate spine members 110, 120.

FIGS. 5-7 depict the embolectomy device 100 of FIG. 4 in perspective three-dimensional views of the device expanded configuration. FIG. 5 depicts the embolectomy device 100 in a perspective side view of the expanded configuration. FIGS. 6-7 depict the embolectomy device 100 in further perspective views of the expanded configuration, such as having the first and second elongate spine members 110, 120 disposed in the same plane of the 3D Cartesian coordinate system, as shown in FIG. 6.

Figure 8:
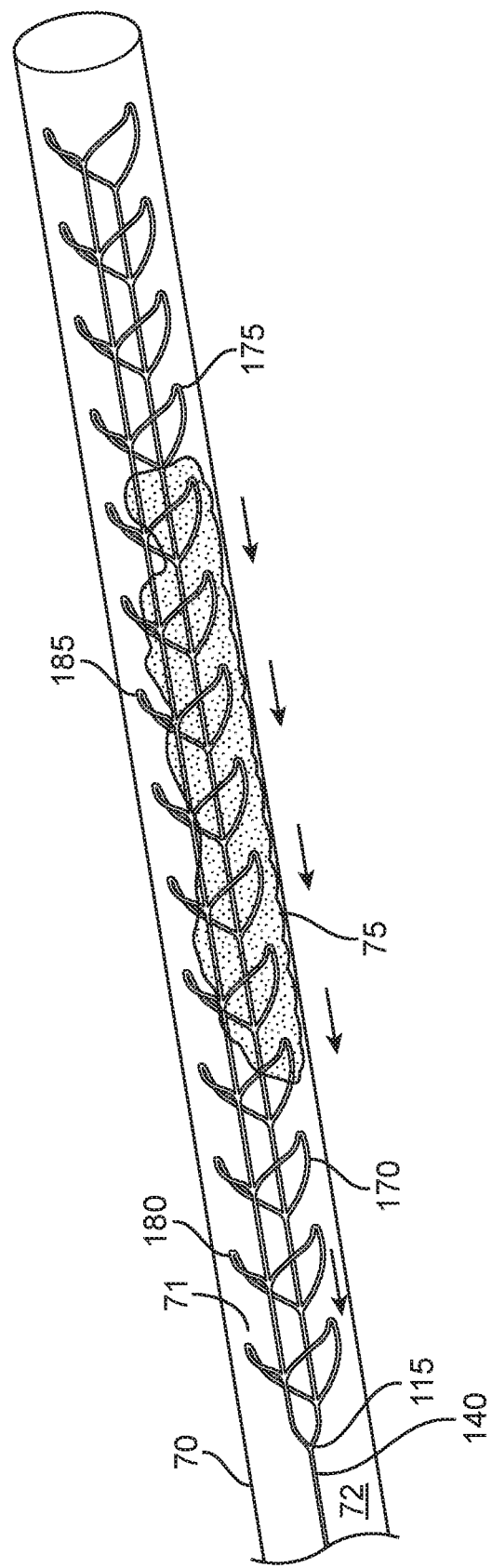
FIG. 8 is an exemplary perspective view depicting integration of the embolectomy device of FIGS. 4-7 with an embolic obstruction.

The embolectomy device 100 comprises an antenna 115 (FIGS. 5-8) at proximal end portion L6 (FIG. 4). The antenna 115 is formed by the respective proximal ends of the first and second elongates spine members 110, 120 coupled together by solder, weld, adhesive, or other suitable attachment methods. The antenna 115 is further coupled to an elongate pusher wire 140 that extends proximally from the embolectomy device 100. The antenna 115 is coupled to the pusher wire 140 by a solder, weld, adhesive, or other suitable attachment methods. The pusher wire 140 is configured to advance and withdraw the embolectomy device 100 through sheaths and/or catheters into a target site in a blood vessel 70 (FIG. 8). The embolectomy device 100 comprises a delivery constrained configuration to be translated through sheaths and/or catheters (not shown), and a deployed expanded configuration when the embolectomy device 100 is not radially constrained (FIGS. 5-7).

Further, as shown in FIGS. 5-7, the attachments between the first plurality of clot engaging structures 170 to the respective first and second elongate spine members 110, 120 are symmetrically disposed with respect to the attachments between the second plurality of clot engaging structures 180 to the respective first and second elongate spine members 110, 120, such that the pointed regions 175, 185 flared outwardly with respect to the each other. In the expanded configuration of the embolectomy device 100, the symmetrically disposed first and second plurality of clot engaging structures 170, 180 having opposite facing chevron/furcula-like configurations define, outline or contour a plurality of "jaw-like" structures 190 along the length L5 of the device 100, as depicted in FIGS. 5-7. The pointed regions 175, 185 of the respective first and second plurality of clot engaging structures 170, 180 are distally oriented, such as each of the "jaw-like" structures 190 face towards the distal portion 150 of the embolectomy device 100 to allow re-sheathing of the device 100 within the lumen of a catheter.

Figure 19:
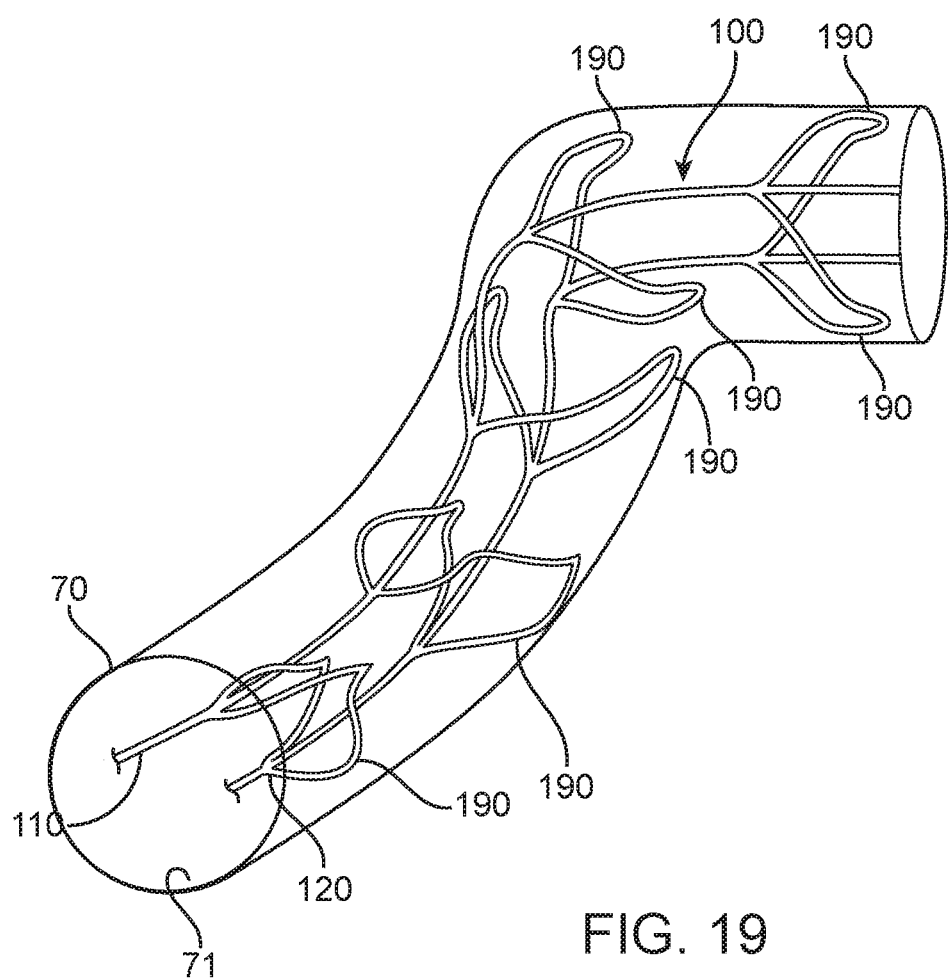
FIG. 19 is a perspective view the embolectomy device of FIGS. 4-8, disposed within a tortuous vasculature.

Due to the symmetry of the respective clot engaging structures of the first plurality 170 and of the second plurality 180 of the embolectomy device 100, when the device expands within a blood vessel 70 having a clot 75, the device 100 orients itself on a neutral axis of turn by the force exerted by one of the plurality of the clot engaging structures 180, against the wall 71 or inner surface of the blood vessel 70, as shown in FIG. 19. Further, due to the symmetry of the embolectomy device 100, the first and second elongate spine members 110, 120 tend to bend and align the device 100 with the neutral axis as the device 100 as is translated (advanced or withdrawn) through the catheter or blood vessel. The first and second elongate spine members 110, 120 tendency towards bending and aligning with the neutral axis as the device 100 (FIG. 19) allows, permits or ensures the alignment of the jaw-like structures 190 of the embolectomy device 100 with the embolic obstruction 75 when the device 100 is deployed, such that the first and second elongate spine members 110, 120 are disposed laterally to the obstruction (FIG. 8 and FIGS. 20C-D).

FIG. 8 and FIGS. 20A-D illustrates an exemplary use of the embolectomy device 100 according to the disclosed inventions. FIGS. 20A-D are cross-sectional views of the exemplary use of the embolectomy device 100 disposed within the lumen 72 of the blood vessel 70. In an unexpanded or radially compressed configuration, such as when the embolectomy device 100 is disposed within a delivery catheter 80 (FIGS. 20A-B), the embolectomy device 100 has an unexpanded outer diameter (UOD) between 0.4 to 0.7 millimeters. In a radially expanded configuration (FIGS. 5-8 and FIG. 20D), the embolectomy device 100 comprises an expanded outer diameter (EOD) between 1.5 to 10 millimeters. FIG. 8 is a perspective view of the blood vessel 70 having lumen 72 with the embolic obstruction 75 therein, and the embolectomy device 100 engaging the obstruction/clot 75. The respective clot engaging structures of the first plurality 170 and of the second plurality 180 forming the "jaw-like" structures 190 of the embolectomy device 100 of FIGS. 4-8 are resilient and configured such that, when the embolectomy device 100 is unsheathed within in a blood vessel 70 alongside a clot 75, the clot engaging structures of one of the first 170 and second 180 plurality contact and compress against a wall 71 of the blood vessel to provide a biasing force to facilitate engagement of the clot engaging structures of the other one of the first and second plurality 170, 180 with the clot 75, as it will be described in further detail below.

Figure 20A:
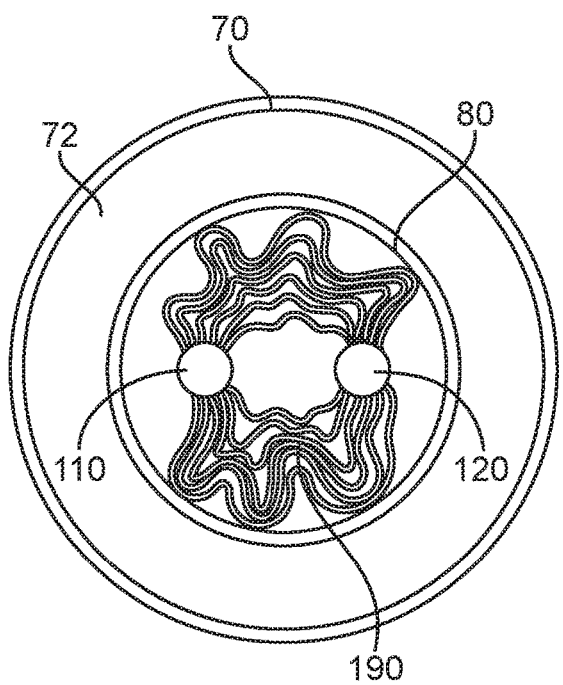
FIGS. 20A-20D are cross-sectional views of exemplary use of the embolectomy device of FIGS. 4-8, according to embodiment of the disclosed inventions.
Figure 20B:
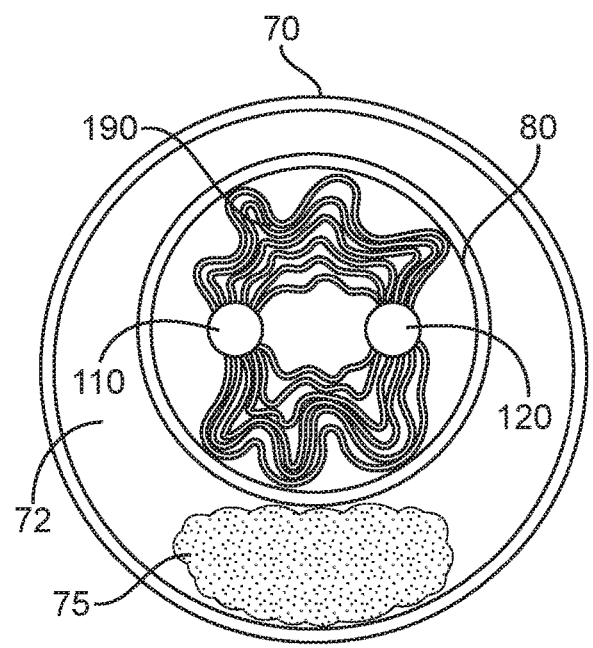
Figure 20C:
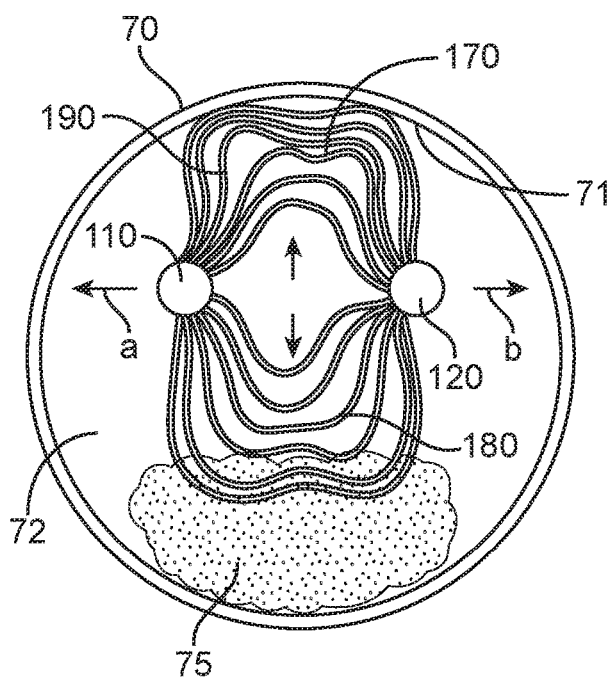
Figure 20D:
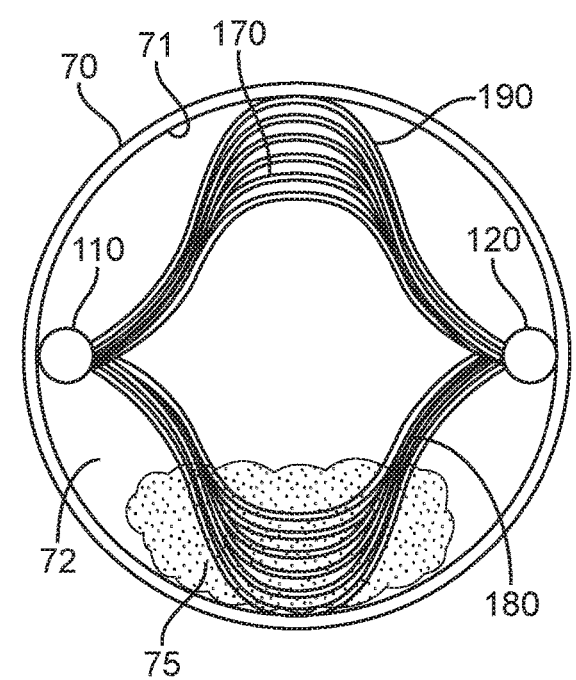

FIG. 20B depicts the embolectomy device 100 disposed within the delivery catheter 80, while the catheter 80 is adjacently disposed to the embolic obstruction/clot 75. When embolectomy device 100 is advanced out the catheter 80, and/or the catheter 80 is withdrawn proximally relative to the device 100 (or some of each) into the blood vessel 70 (FIG. 20C), the respective first and second elongate spine members 110, 120 are configured to outwardly translate (shown by arrows a and b of FIG. 20C) while the "jaw-like" structures 190 is configured to radially expand. As shown in the exemplary FIGS. 20C-D, the radial expansion of the "jaw-like" structures 190 cause the first 170 plurality of clot engaging structures to contact and compress against a wall 71 of the blood vessel providing a biasing force that facilitates engagement of the second 180 plurality of clot engaging structures with the embolic obstruction/clot 75. Further, the pushing force exerted by the plurality of clot engaging structures 180 against the wall 71 of the blood vessel 70 allows the first and second spine members 110 and 120 to extend or wrap around the clot 75 while allowing the other plurality of clot engaging structures 170 to engage, snare, integrate, capture and/or entrap clot 75 (FIG. 20D). When the device 100 expands from the constricted configuration, the respective "jaw-like" configuration 190 of the embolectomy devices 100 produce sufficient outwardly and/or radial force (e.g., radial force per unit length of between 0.005 N/mm to 0.10 N/mm, preferable between 0.040 N/mm to 0.080 N/mm when the outer diameter of the main body portion is between 1.0 mm to 1.5 mm, and preferably between 0.010 N/mm to 0.035 N/mm when the diameter of the main body portion is approximately 3.0 mm) to snare, engage and/or otherwise capture an obstruction in the vasculature.

FIGS. 9-12 illustrate an embolectomy device 200, constructed in accordance with other embodiments of the disclosed inventions. Similar to device 100 of FIGS. 4-8, the embolectomy device 200 may be formed of a unitary component or may include separate components that are welded, bonded or otherwise coupled to one another, as previously disclosed. By way of a non-limiting example of the device when formed of a unitary component, the two-dimensional plane view of FIG. 9 may be used as a cut pattern; such as, placing the pattern over and/or around a tubular structure to manufacture the embolectomy device 200 by laser cutting said pattern into the tubular structure. The embolectomy device 200 comprises self-expanding and/or shape memory materials, such as Nitinol, or other suitable materials or combinations thereof, and further includes a delivery constrained configuration and a deployed expanded configuration FIGS. 9-12.

Similar to the embolectomy device 100 of FIGS. 4-8, the embolectomy device 200 of FIGS. 9-12 comprises a first elongate spine member 210 extending along the longitudinal axis 230, and a second elongate spine member 220 extending along the longitudinal axis 230 and disposed substantially parallel to the first elongate spine 210. The embolectomy device 200 having a first plurality of clot engaging structures 270, each clot engaging structure 270 of the first plurality 270 having a first end 272 attached to the first elongate spine member 210 and a second end 274 attached to the second elongate spine member 220. The embolectomy device 200 further having a second plurality of clot engaging structures 280, each clot engaging structure 280 of the second plurality having a first end 282 attached to the first elongate spine member 210 at a location in which the first end 272 of a corresponding clot engaging structure 270 of the first plurality is attached to the first elongate spine member 200, and a second end 284 attached to the second elongate spine member 220 at a location in which the second end 274 of the corresponding clot engaging structure of the first plurality 270 is attached to the second elongate spine member 220.

The first elongate spine member 210 and the second elongate spine member 220 of the embolectomy device 200 of FIGS. 9-12, each have an overall length L8 of approximately 32 millimeters with respective active portions length L9 measuring approximately 30 millimeters, and a proximal end portion length L10. The active portion length L9 of the spine members 210 and 220 includes the first and second plurality of clot engaging structures 270, 280. The proximal end portion L10 includes the coupled respective proximal ends of the first and second elongates spine members 210 and 220 forming the antenna 215. The proximal end portion L10 measures approximately 0.1 to 1.0 millimeters. The first elongate spine member 210 and the second elongate spine member 220 are composed of suitable stretch-resistance material having substantially the same mass (e.g., width and/or thickness) along their respective length L8. In some embodiments, the mass (e.g., width and/or thickness) along the respective length L8 of the first and/or second elongate spine members 210, 220 may vary, similarly to the previously described spine members 110 and 120.

Figure 9:
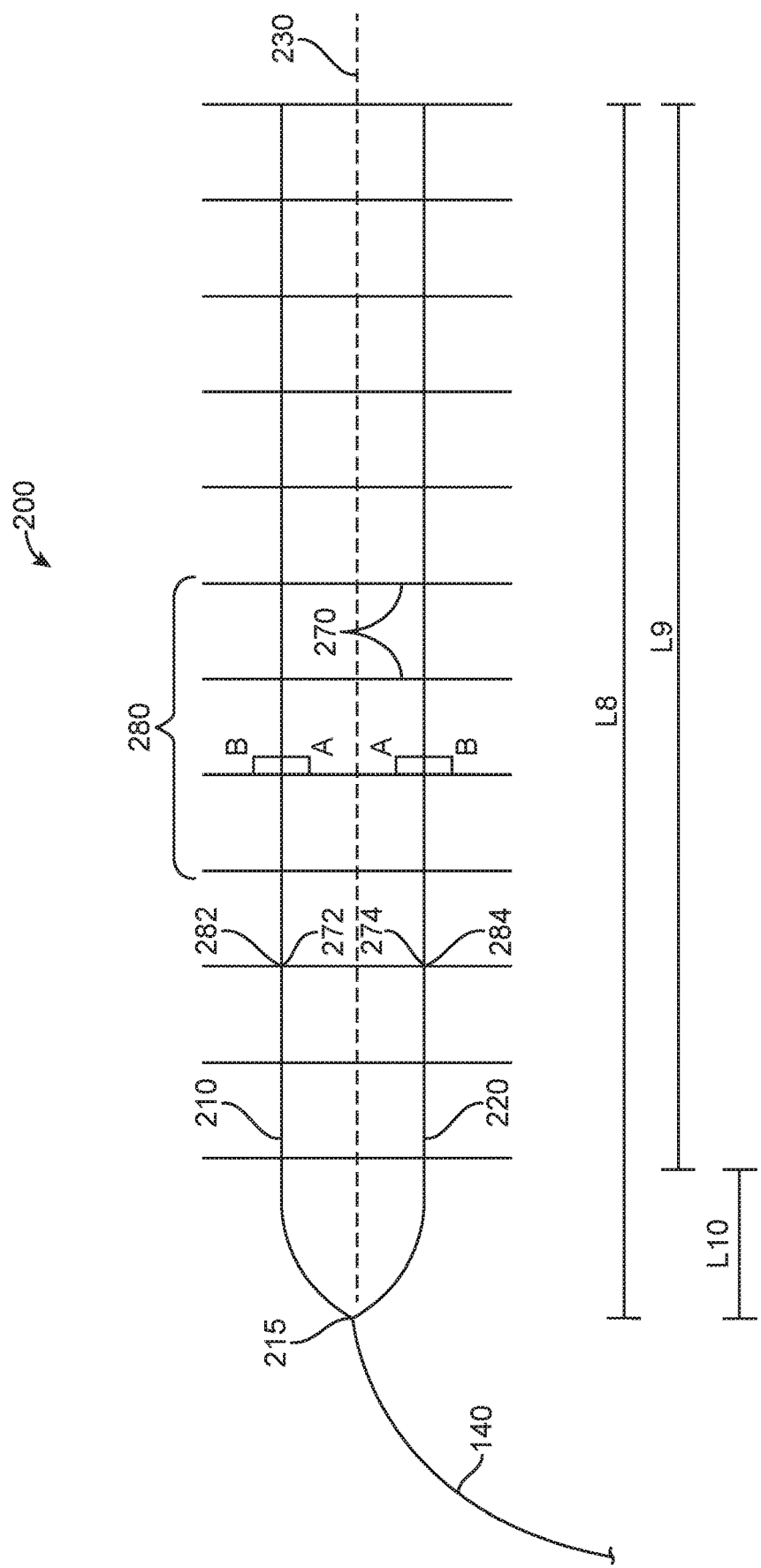
FIG. 9 is a planar and cross-sectional view of an exemplary embolectomy device constructed according to another embodiment of the disclosed inventions.
Figure 10:
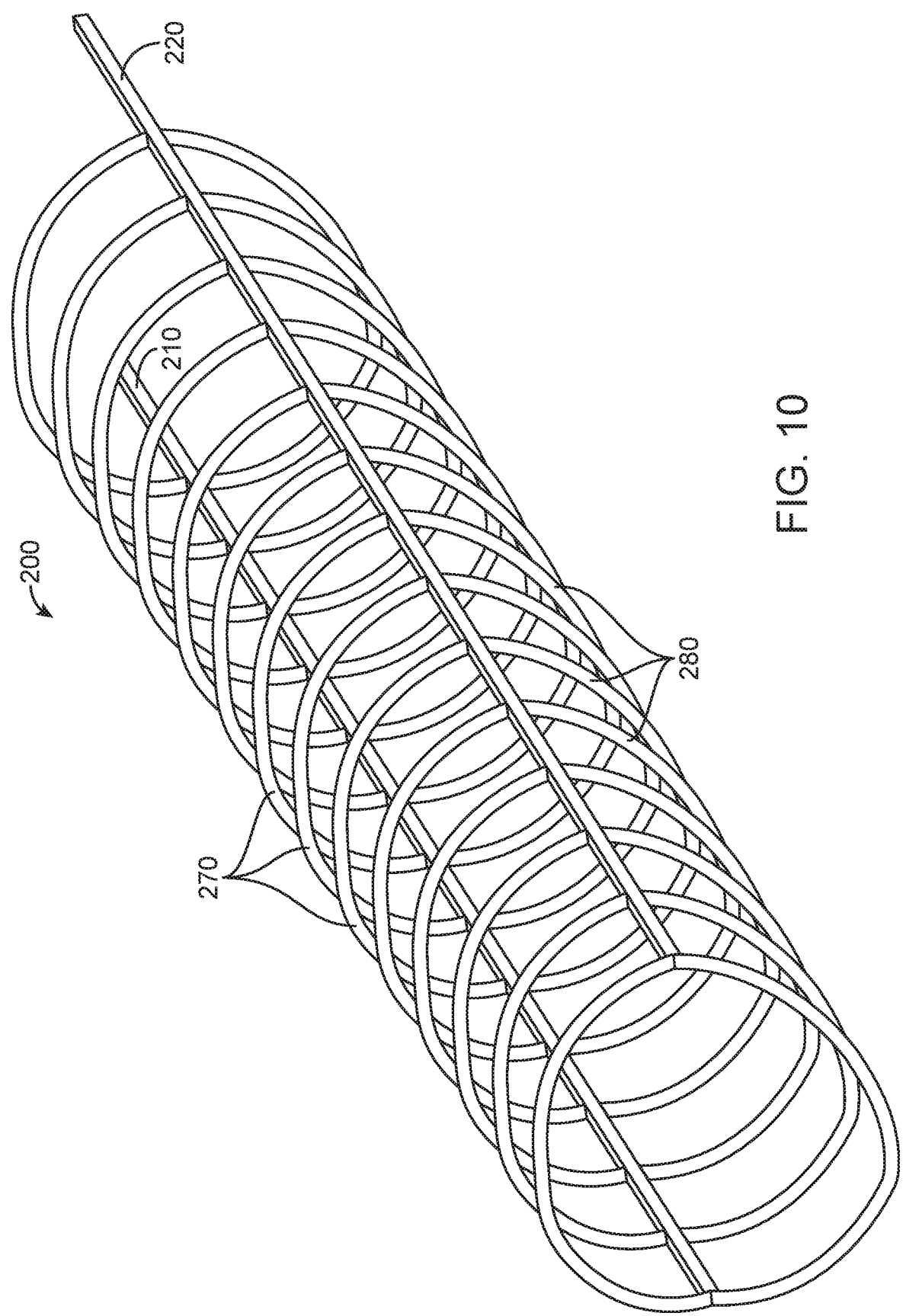
FIGS. 10-12 are perspective views of the device of FIG. 9, according to the disclosed inventions.
Figure 11:
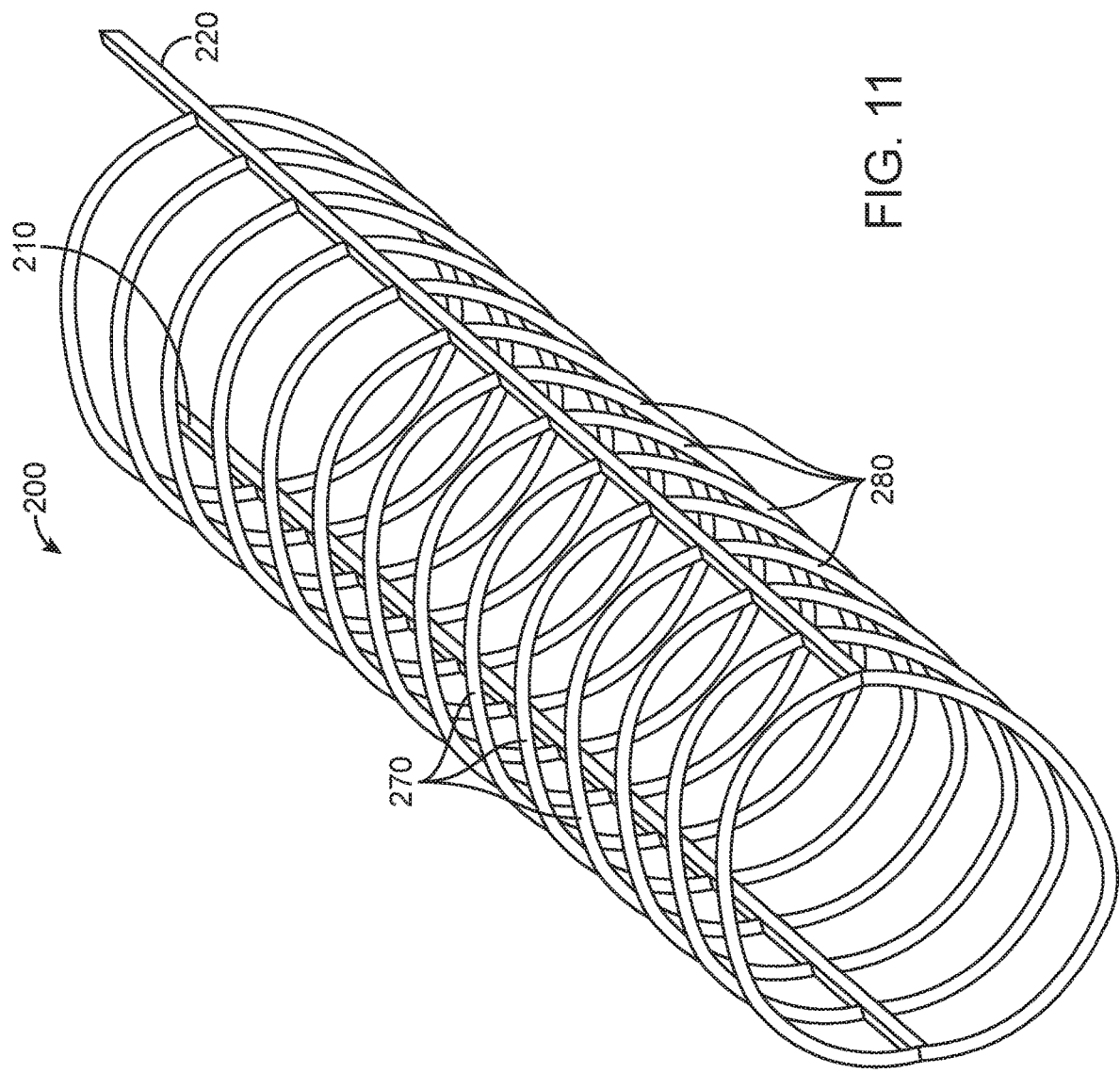
Figure 12:
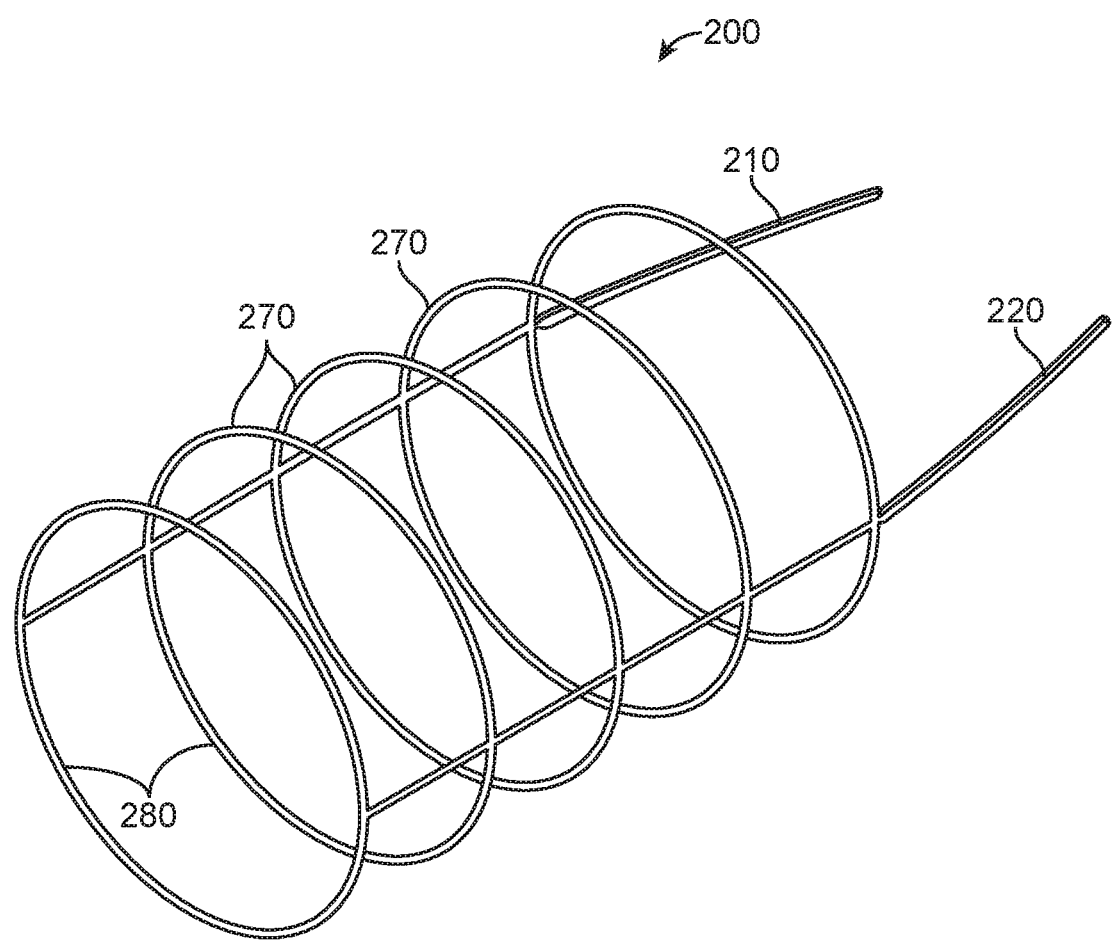

By way of non-limiting example, the embolectomy device 200 comprises clot engaging structures 270 in the first plurality of structures 270, and clot engaging structures 280 in the second plurality of structures 280, as shown in FIG. 9. However, it should be appreciated than the first and second plurality of structures 270 and 280 may have between 5 (FIG. 12) to 45 (not shown) clot engaging structures extending along the length L9 or attached to the respective first and second elongate spine members 210, 220. In the embodiments of FIGS. 9-12, each of the first and second plurality of structures 270 and 280 may be closely disposed with respect to each, as to include more structures within the embolectomy device, as compared to the embodiments of FIGS. 4-8. The cross-sectional views along the length of one or more of the clot engaging structure 270 and/or 280 may be include a continuous configuration or may vary along their respective length. For example, a cross-section of one of the clot engaging structure 270 can be circular in a first portion and can be oval in a second portion (not shown). Further, the cross-sectional views along the along the length of one or more of the clot engaging structure 270 and/or 280 may include round, oval, square or any other suitable cross-sectional configuration or combination thereof.

Similar to the embolectomy device 100 of FIGS. 4-8, the embolectomy device 200 of FIGS. 9-12, may include radiopaque markers or be coated with a layer of radiopaque materials, and comprises an antenna 215 coupled to an elongate pusher wire 140 that extends proximally from the embolectomy device 200. The antenna 215 is coupled to the pusher wire 140 by a solder, weld, adhesive, or other suitable attachment methods. The pusher wire 140 is configured to advance and withdraw the embolectomy device 100 through sheaths and/or catheters into a target site in a blood vessel.

One difference from the device 100 is that the embolectomy device 200 is that each of the first ends 272 of each of the clot engaging structures 270 are substantially orthogonally disposed and attached to the first elongate spine member 210, and the second end 274 are substantially orthogonally disposed and attached to the second elongate spine member 220, as shown by exemplary angles "A" in FIG. 9. Further, each of the first ends 282 attached of the second clot engaging structures 280 are substantially orthogonally disposed and attached to the first elongate spine member 210, and the second end 284 are substantially orthogonally disposed and attached to the second elongate spine member 220, as shown by exemplary angles "B" in FIG. 9 Another difference from the device 100 is that the substantially orthogonal attachments of the clot engaging structures 270 and 280 to their respective first and second elongate spine members 210 and 220 in the device 200 form curved rib-like configurations of the clot engaging structures 270 and 280, as better appreciated in FIGS. 10-12, instead of having the chevron/furcula-like configuration of FIGS. 5-8.

Figure 13:
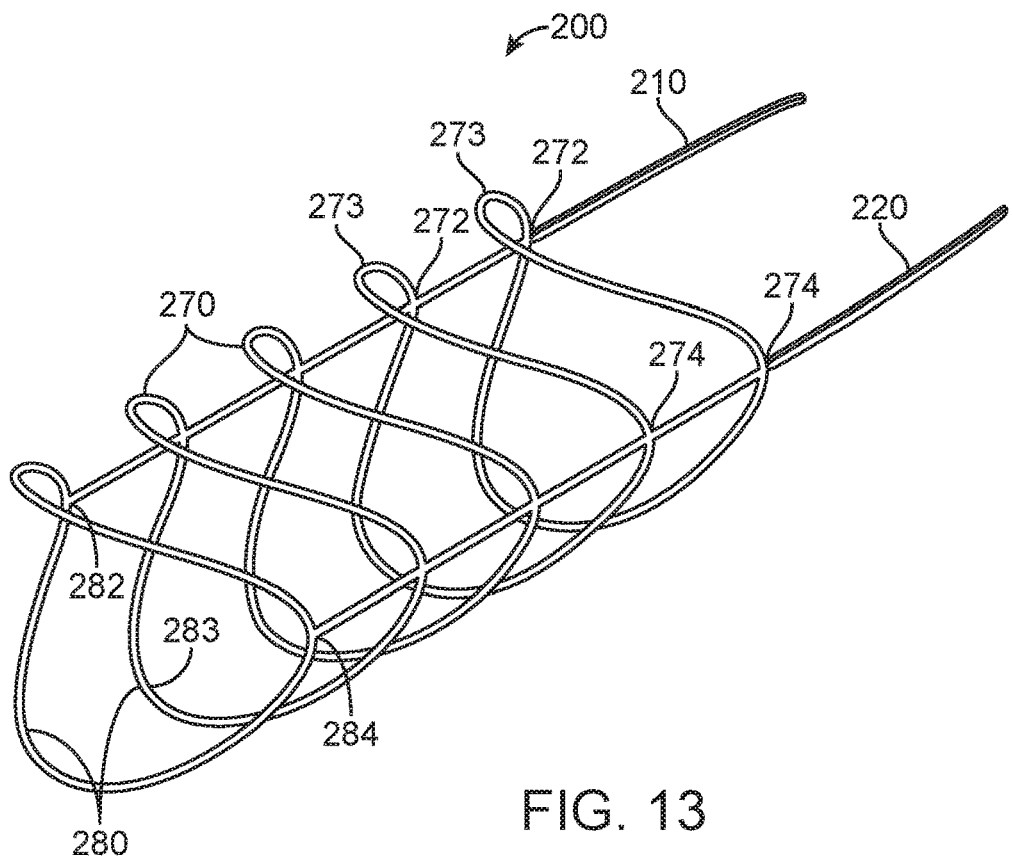
FIGS. 13-14 are exemplary embolectomy devices constructed according to an alternative embodiment of the disclosed inventions of the device of FIG. 9, in a radially expanded configuration.

FIGS. 13-16 illustrate alternative embodiments of the embolectomy device 200, constructed in accordance with other embodiments of the disclosed inventions. In the embodiments of FIGS. 13-16, the curved rib-like configurations of the first and second plurality of clot engaging structures 270 and 280 of the embolectomy device 200 are distally disposed. The distally disposed first and second plurality of clot engaging structures 270 and 280 are configured to engage, snare, capture and/or entrap the embolic obstruction 75 disposed within the blood vessel 70, and/or to facilitate re-sheathing of the embolectomy device 200 within the lumen of sheaths or catheters. As shown in FIG. 13, the first plurality of clot engaging structures 270 is distally disposed as each of the clot engaging structures 270 comprises a middle portion 273 disposed between the first end 272 attached to the first elongate spine member 210 and the second end 274 attached to the second elongate spine member 220, where the middle portion 273 is distally disposed with respect to either the first end 272 and second end 274. Further, as shown in FIG. 13, the second plurality of clot engaging structures 280 is distally disposed as each of the clot engaging structures 280 comprises a middle portion 283 disposed between the first end 282 attached to the first elongate spine member 210 and the second end 284 attached to the second elongate spine member 220, where the middle portion 283 is distally disposed with respect to either the first end 282 and second end 284.

It should be appreciated that the curved rib-like configurations of the first and second plurality of clot engaging structures 270 and 280 of the embolectomy device 200 extend outwardly in their deployed configuration when unsheathed out of the delivery catheter 80. Then, the clot engaging structures 270 and 280 may remain neutral along the longitudinal axis 230. In an alternative embodiment, the clot engaging structures 270 and 280, particularly their respective middle portions 273 and 283 may extend inwardly towards the axis 230, similarly to the embodiments of FIGS. 5-8. Further alternative embodiments of the directional orientation of the respective middle portions 273 and 283 can be manufactured to increase or decrease interaction with the obstruction/clot 75 or blood vessel 72 as desired. For example, having neutral middle portions 273 and 283 of the device 200 directed towards the clot and inward middle portions 273 and 283 beyond the location of clot may be desirable.

Figure 14:
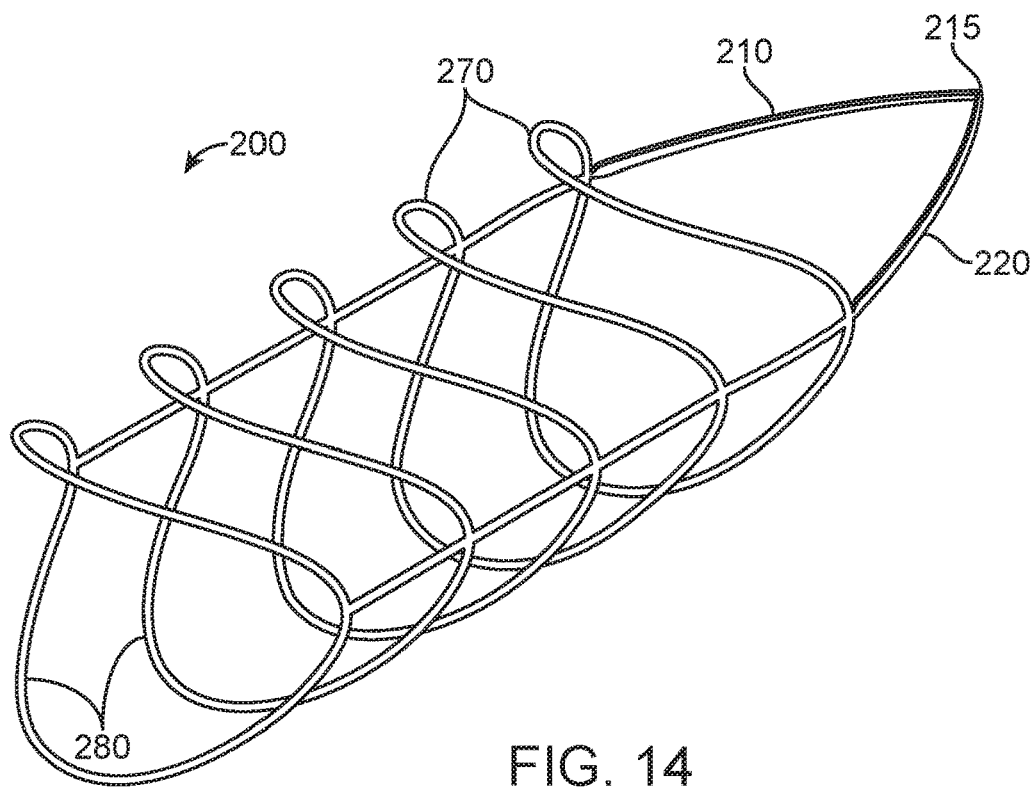
Figure 15:
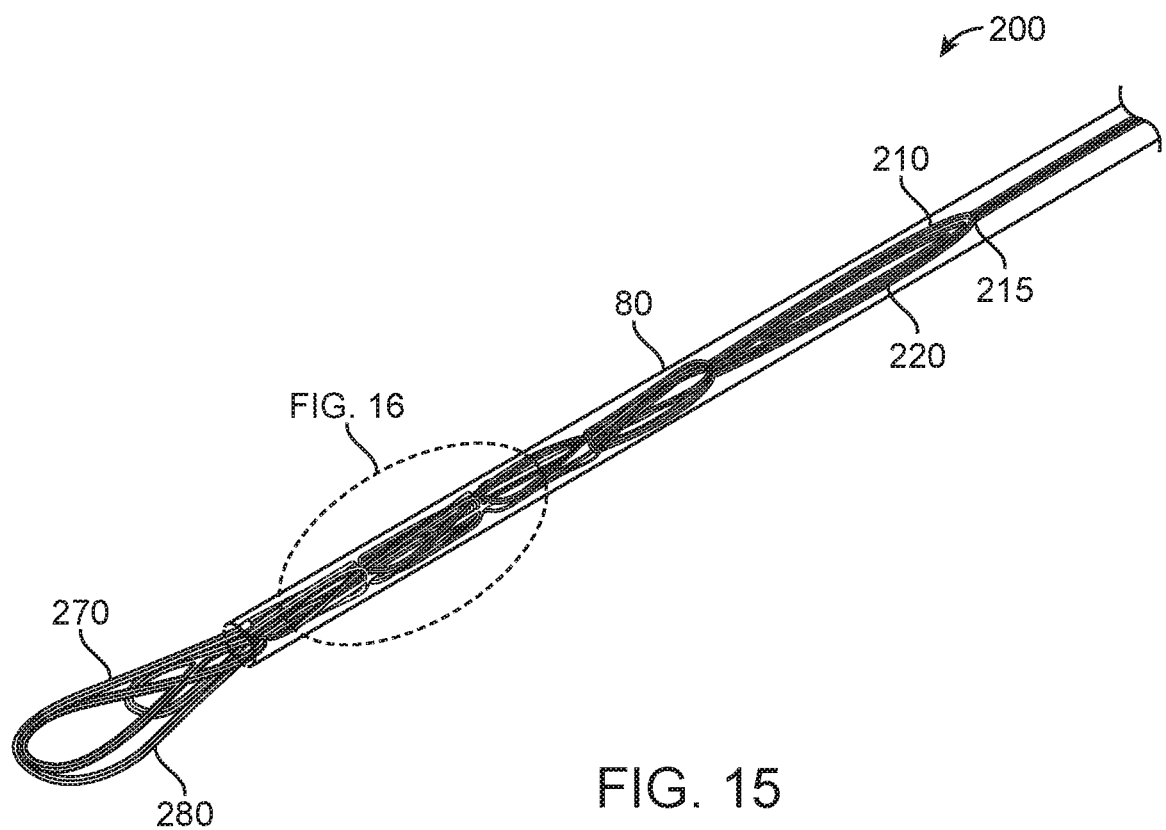
FIG. 15 is a perspective view of the devices of FIGS. 13-14 in a radially constrained configuration.
Figure 16:
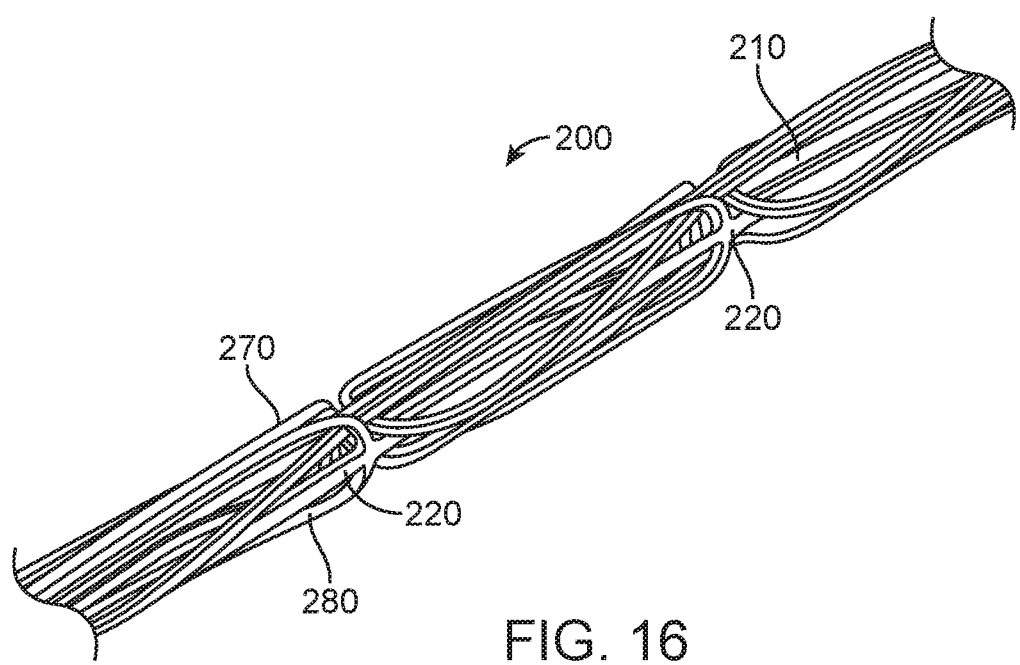
FIG. 16 is a detailed perspective view of the device of FIG. 15, according to the disclosed inventions.

FIGS. 13-14 illustrate the distally disposed first and second plurality of clot engaging structures 270 and 280 of the embolectomy device 200 in the radially expanded configuration, and FIG. 14 further illustrate the antenna 215 embolectomy device 200 where the spines 210 and 220 are joint and configured to be coupled to the elongate pusher wire (not shown) that extends proximally from the embolectomy device 200. FIG. 15 illustrate the distally disposed first and second plurality of clot engaging structures 270 and 280 of the embolectomy device 200 in the radially constrained configuration, having the clot engaging structures 270 and 280 overlap when the embolectomy device 200 is radially constrained (e.g., by catheter 80). The distally and symmetrically disposed clot engaging structures 270 and 280 allows for overlapping of the structures, facilitating capturing of embolic obstructions and re-sheathing of the embolectomy device 200. FIG. 16 illustrates a detailed view of a portion of the radially constrained embolectomy device 200 of FIG. 15.

Similar to the embodiments of FIGS. 4-8, due to the symmetry of the respective clot engaging structures of the first plurality 270 and of the second plurality 270 of the embolectomy device 200 of FIGS. 9-16, when the device 200 expands within a blood vessel having a clot, the device 200 orients itself on a neutral axis of turn by the force exerted by one of the plurality of the clot engaging structures, against the wall or inner surface of the blood vessel. Further, the pushing force exerted by the one of the plurality of clot engaging structures against the wall of the blood vessel allows the first and second spine members 210 and 220 to extend or wrap around the clot while allowing the other/opposed plurality of clot engaging structures to engage, snare, integrate, capture and/or entrap the clot.

Figure 1B:
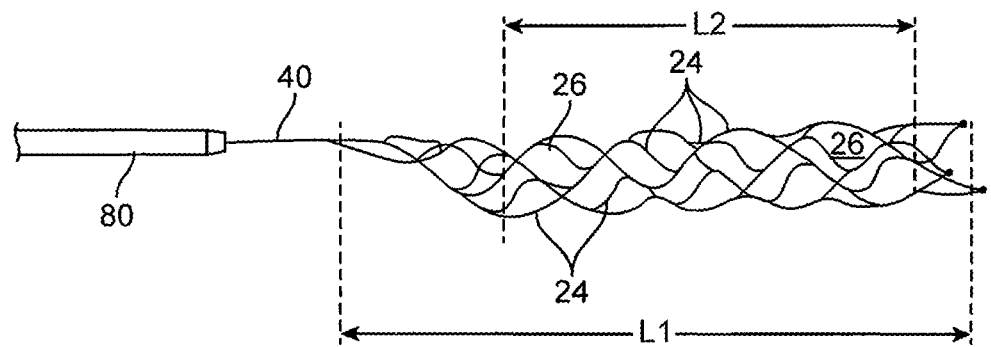
Figure 2:
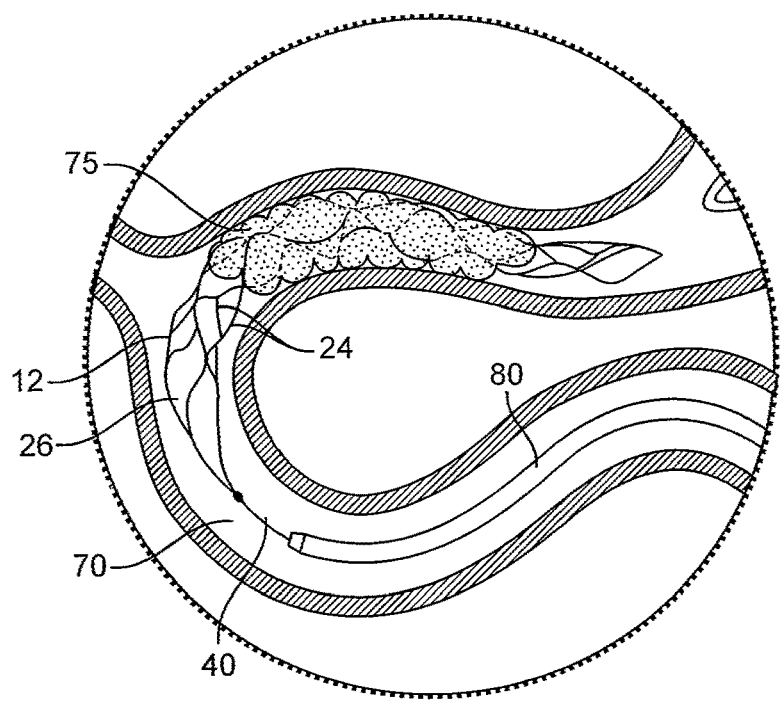
FIG. 2 is a cross-sectional view of the prior art embolectomy device depicted in FIGS. 1A-1B, shown while capturing an embolic obstruction within a blood vessel.
Figure 3A:
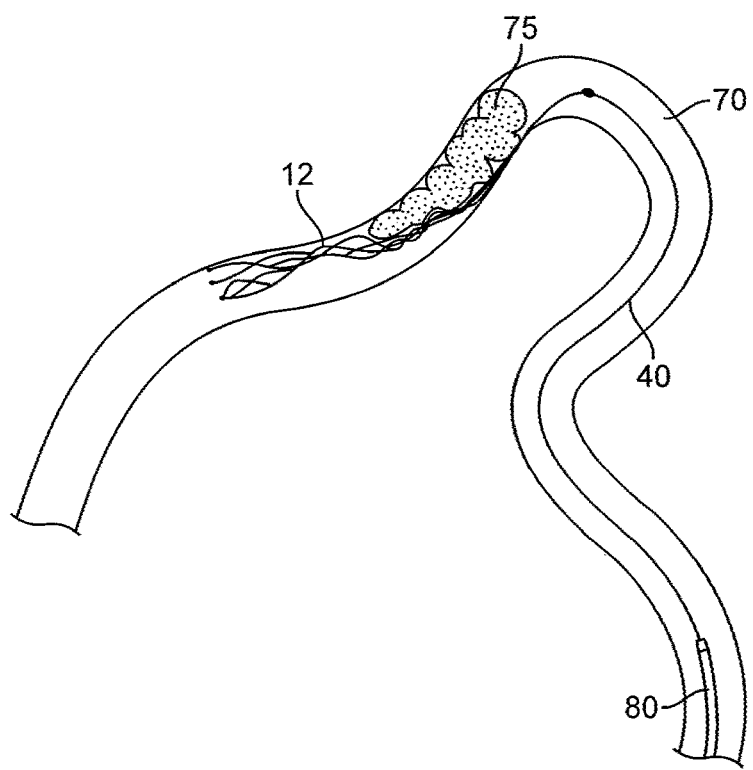
FIG. 3A is a perspective view and FIGS. 3B-3G are cross-sectional views of the prior art embolectomy device of FIGS. 1A-1B, shown positioned within a blood vessel adjacent to an embolic obstruction.
Figure 3D:
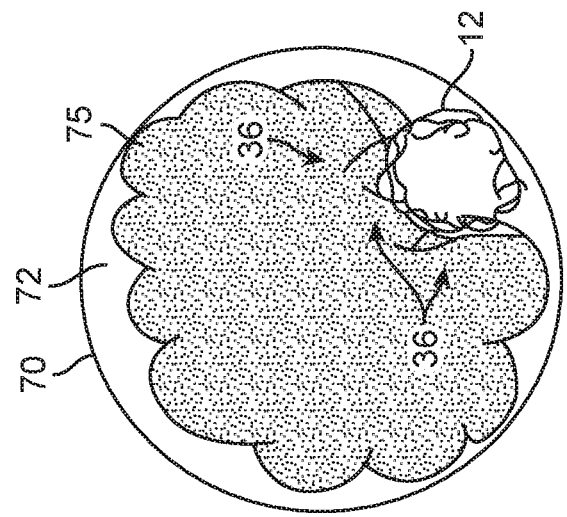
Figure 3C:
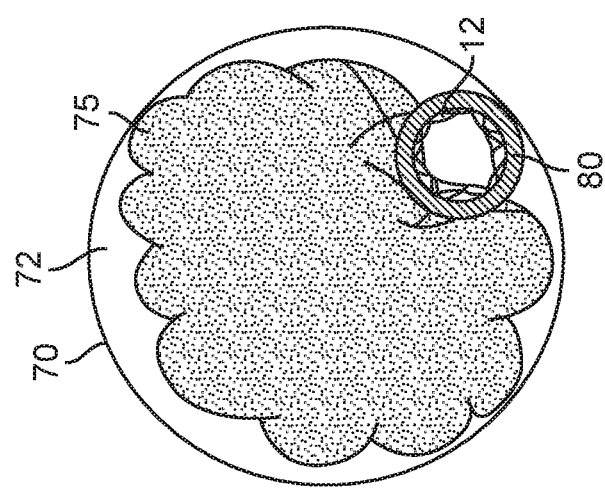
Figure 3B:
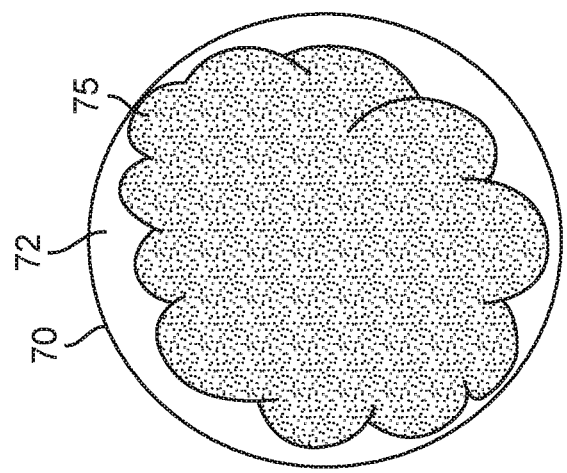
Figure 3G:
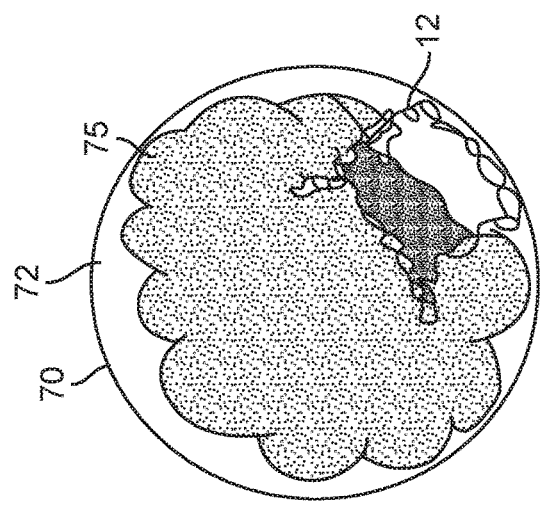
Figure 3F:
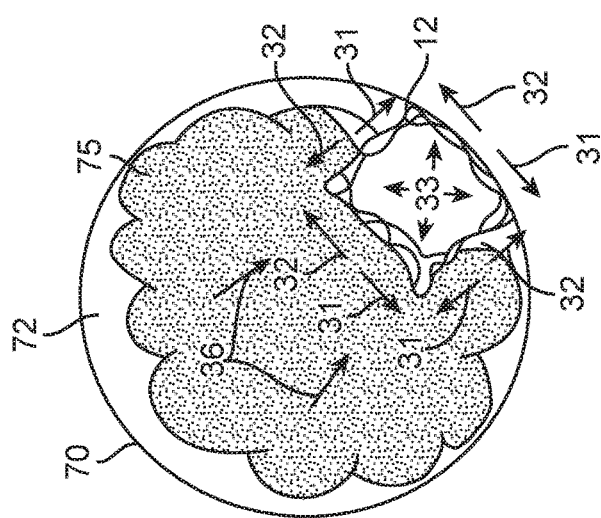
Figure 3E:
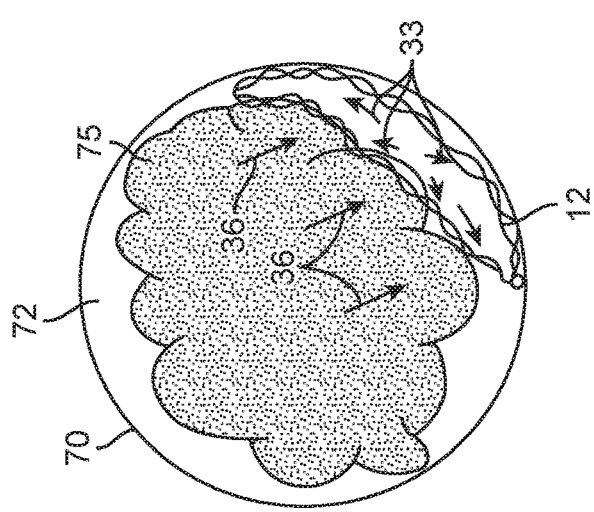
Figure 17:
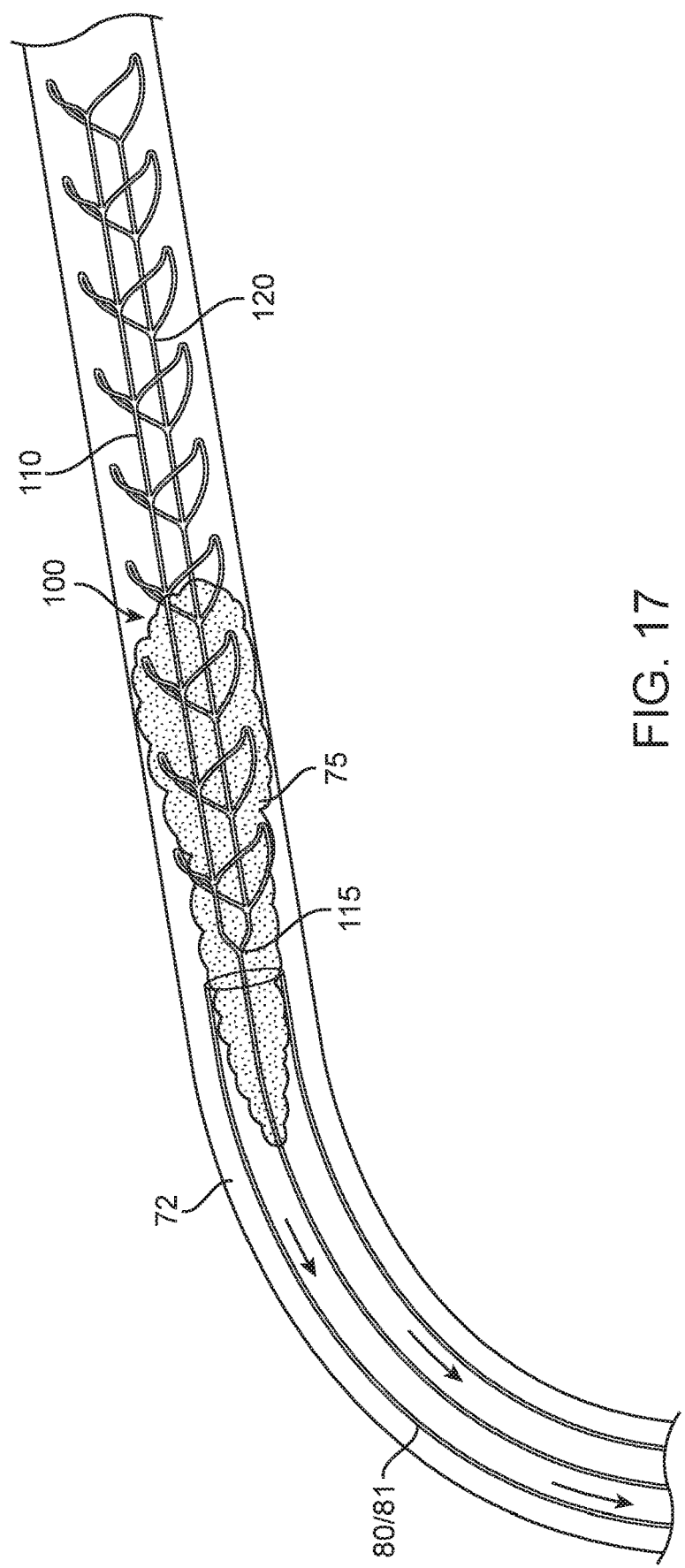
FIG. 17 is a perspective view of the use of the device of FIGS. 4-7 with an aspiration catheter, according to the disclosed inventions.

It will be appreciated that the embolectomy devices 100 and 200 of FIGS. 4-16 are configured to facilitate deployment accuracy within a target site of a patient and facilitate removal of the obstruction/clot, due to relative short proximal taper and substantially less mass at the proximal end portions L6/L10 of the devices 100/200, as compared to the prior art device of FIGS. 1-2. As shown in FIGS. 4-16, the proximal end portions L6/L10 having antennas 115/215 of the respective embolectomy devices 100/200 comprise the relative short proximal taper and less mass by having just the proximal portions of the first and second spine members 110 and 120. In contrast, the proximal end portion 14 of the device 12 of FIGS. 1-2 has a longer taper and larger mass by having a plurality of struts 24 at portion 14. Referring back to FIGS. 4-16, due to the relative short proximal taper and substantially less mass at the proximal ends portions L6/L10 having antennas 115/215 of the respective embolectomy devices 100 and 200, the embolectomy devices are configured to be paired with a relative large bore aspiration catheter 80/81 to facilitate aspiration, engagement and removal of the clot. In the exemplary embodiment of FIG. 17, an embolectomy device 100 deployed distally to a proximal portion of the clot and in view of the relative short proximal taper and substantially less mass of the proximal end portion L6 having antenna 115 of the device 100, the device 100 produces minimal or insignificant interference with the aspiration catheter 80/81, allowing and facilitating aspiration (depicted by arrows in FIG. 17), engagement and removal of the clot by the aspiration catheter 80/81.

It will be further appreciated that the respective first and second spine members 110 and 120 composed of suitable stretch-resistance material of FIGS. 4-16 enables, allows and/or facilitate the pulling/withdrawal of the jaw-like structures (FIGS. 5-8) or rib-like configurations (FIGS. 10-16) of the respective embolectomy devices 100 and 200 substantially simultaneously with one another (e.g., jaw-like structures or rib-like configurations) when the device 100/200 is withdrawn. The substantially simultaneously pulling/withdrawal of the jaw-like structures or rib-like configurations of the device 100/200 by the spine members 110/120 further enables, allows and/or facilitate the pulling/withdrawal along the entire length of the obstruction/clot 75 (shown by arrows in FIG. 8). The substantially simultaneously pulling/withdrawal along the complete length of obstruction/clot by the embolectomy device 100/200, minimizes and prevents pulling the clot by parts or in series that may produce undesirable consequences, such as breaking the clot into pieces that may dislodge out of the device, or turning, folding or rolling the clot compressing it into a denser mass more difficult to remove out of the vasculature.

Figure 18:
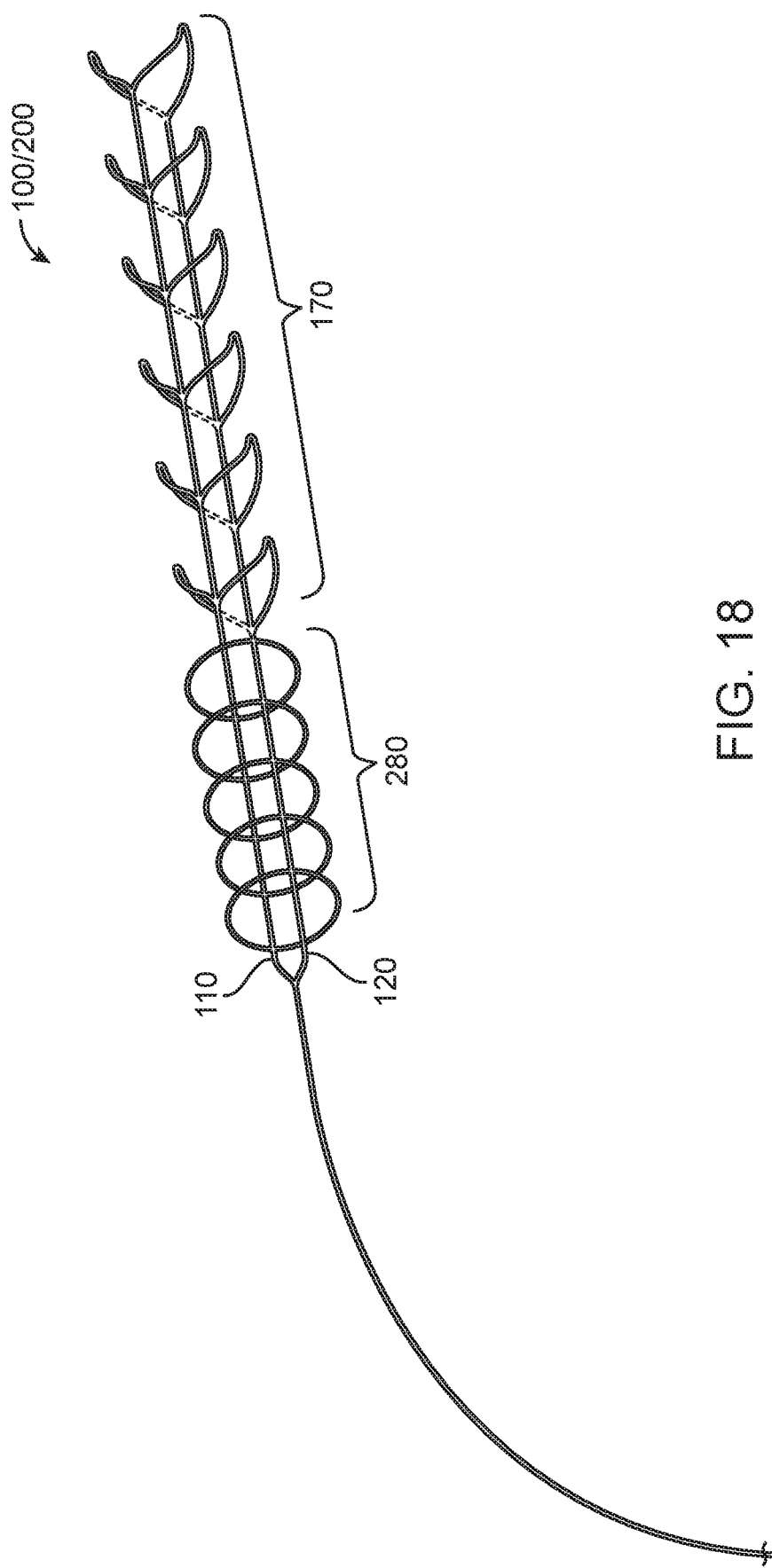
FIG. 18 is a perspective view of an exemplary embolectomy device constructed according to another embodiment of the disclosed inventions.

In some embodiments, the embolectomy device 100/200 may comprise a combination of first and second plurality of clot engaging structures along the length of the first and second spine members 110 and 120. FIG. 18 depicts an exemplary embodiment of an embolectomy device 100/200 having the first plurality of clot engaging structures 280 of FIG. 9-12 or 13-16 disposed at the proximal portion, and having the second plurality of clot engaging structures 170 of FIGS. 4-8 disposed at the distal portion. Further embodiments of the embolectomy device may include other suitable configurations and combinations of the first and second plurality of clot engaging structures as previously disclosed.

It will be appreciated that the embolectomy devices depicted in FIGS. 4-18 may be used in other suitable medical devices, for example, disposed within tubular prosthesis, implants, stents, fluid diverters or the like for both vascular and non-vascular applications. Further, it will be appreciated that combinations of components, features and functions between the embodiments FIGS. 4-18 may be made without departing from the scope of the inventive concepts disclosed herein.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. An elongate embolectomy device biased to expand from a radially constrained configuration to a radially expanded configuration when released from a delivery catheter within a blood vessel, the embolectomy device comprising:
    a first elongate spine member extending along a longitudinal axis of the embolectomy device;
    a second elongate spine member extending along the longitudinal axis of the embolectomy device substantially parallel with the first elongate spine; and
    a plurality of resilient clot engaging arms, each having a curved first portion attached to the first elongate spine member, a curved second portion attached to the second elongate spine member, and a V-shaped middle portion connecting the first curved portion to the second curved portion,
    wherein the respective V-shaped middle portions of the plurality of resilient clot engaging arms form a succession of substantially aligned peaks positioned radially outwardly along the longitudinal axis of the embolectomy device, when the embolectomy device is in the radially expanded configuration.

2. The embolectomy device of claim 1, wherein the plurality of resilient clot engaging arms extend distally at an acute angle relative to the longitudinal axis of the embolectomy device, when the embolectomy device is in the radially expanded configuration.

3. The embolectomy device of claim 1, wherein the respective first and second curved portions of the plurality of resilient clot engaging arms have arcuate configurations.

4. The embolectomy device of claim 1, further comprising a pusher wire, wherein each of the first and second elongate spine members are attached to a distal end portion of the pusher wire.

5. The embolectomy device of claim 4, wherein the first and second elongate spine members are composed of a stretch-resistant material and are configured such that, when the pusher wire is translated proximally within the blood vessel, the respective resilient clot engaging arms are simultaneously translated proximally with the first and second elongate spine members for facilitating engagement of the plurality of resilient clot engaging arms with the clot.

6. The embolectomy device of claim 1, wherein the first and second elongate spine members are configured to bend and align the embolectomy device along a longitudinal neutral axis as the embolectomy device is translated, advanced or withdrawn within the delivery catheter or within the blood vessel.

7. The embolectomy device of claim 1, wherein the plurality of resilient clot engaging arms are a first plurality of resilient clot engaging arms, the embolectomy device further comprising a second plurality of resilient clot engaging arms, each having a curved first portion attached to the first elongate spine member, a curved second portion attached to the second elongate spine member, and a V-shaped middle portion connecting the first curved portion to the second curved portion,
    wherein the respective V-shaped middle portions of the second plurality of resilient clot engaging arms form a succession of substantially aligned peaks positioned radially outwardly along the longitudinal axis of the embolectomy device, when the embolectomy device is in the radially expanded configuration, and wherein the respective V-shaped middle portions of the first plurality of resilient clot engaging arms are circumferentially offset approximately 180° from the respective V-shaped middle portions of the second plurality of resilient clot engaging arms.

8. The embolectomy device of claim 7, wherein the respective resilient clot engaging arms of the first and second pluralities of resilient clot engaging arms are configured such that, when the embolectomy device is unsheathed within the blood vessel alongside a clot, the resilient clot engaging arms of one of the first and second plurality of resilient clot engaging arms contact and compress against a wall of the blood vessel to provide a biasing force to facilitate engagement of the resilient clot engaging arms of the other one of the first and second plurality of resilient clot engaging arms with the clot.

* * * * *